(12) United States Patent
Wang et al.

(10) Patent No.: US 8,430,055 B2
(45) Date of Patent: Apr. 30, 2013

(54) METHODS AND APPARATUSES FOR COATING BALLOON CATHETERS

(75) Inventors: Jeffrey Wang, Chanhassen, MN (US); Harrison Malinoff, Minneapolis, MN (US); Lixiao Wang, Medina, MN (US); Christopher M. Barry, Medina, MN (US); Dennis W. Wahr, Minnetonka, MN (US); Scott R. Naisbitt, Minneapolis, MN (US)

(73) Assignee: Lutonix, Inc., New Hope, MN (US)

( * ) Notice: Subject to any disclaimer, the term of this patent is extended or adjusted under 35 U.S.C. 154(b) by 765 days.

(21) Appl. No.: 12/549,180

(22) Filed: Aug. 27, 2009

(65) Prior Publication Data

US 2010/0055294 A1 Mar. 4, 2010

Related U.S. Application Data

(60) Provisional application No. 61/092,872, filed on Aug. 29, 2008.

(51) Int. Cl.
*B05C 1/06* (2006.01)
*B05C 5/00* (2006.01)
*B05B 13/04* (2006.01)

(52) U.S. Cl.
USPC ............ 118/261; 118/320; 118/665; 118/307

(58) Field of Classification Search .................. 118/320, 118/665, 261, 203, 249, 246, 305, 307, 321, 118/323, 679–682, 686, 687, 697; 427/2.24, 427/2.25, 2.21, 2.28, 2.1, 2.3, 426; 623/1.42–1.46
See application file for complete search history.

(56) References Cited

U.S. PATENT DOCUMENTS

| | | |
|---|---|---|
| 3,929,992 A | 12/1975 | Sehgal et al. |
| 3,993,749 A | 11/1976 | Sehgal et al. |
| 4,316,885 A | 2/1982 | Rakhit |
| 4,364,921 A | 12/1982 | Speck et al. |
| 4,921,483 A | 5/1990 | Wijay et al. |
| 5,023,262 A | 6/1991 | Caufield et al. |

(Continued)

FOREIGN PATENT DOCUMENTS

| | | |
|---|---|---|
| DE | 101 15 740 | 10/2002 |
| EP | 0 519 063 | 12/1992 |

(Continued)

OTHER PUBLICATIONS

International Search Report for International Application No. PCT/2007/024108, dated Nov. 20, 2008, Examiner Tatjana John.

(Continued)

*Primary Examiner* — Yewebdar Tadesse
(74) *Attorney, Agent, or Firm* — Dinsmore & Shohl LLP

(57) ABSTRACT

Embodiments of the invention relate to a method and apparatus for coating a medical device. In one embodiment, the method for preparing a substantially uniform coated medical device includes (1) preparing a coating solution comprising a solvent, a therapeutic agent, and an additive; (2) loading a metering dispenser with the coating solution; (3) rotating the medical device about the longitudinal axis of the device and/or moving the medical device along the longitudinal or transverse axis of the device; (4) dispensing the coating solution from the metering dispenser onto a surface of the medical device and flowing the coating solution on the surface of the medical device while the medical device is rotating and/or linearly moving; and (5) evaporating the solvent, forming a substantially uniform coating layer on the medical device.

12 Claims, 3 Drawing Sheets

U.S. PATENT DOCUMENTS

| | | | |
|---|---|---|---|
| 5,023,263 A | 6/1991 | Von Burg | |
| 5,023,264 A | 6/1991 | Caufield et al. | |
| 5,026,607 A | 6/1991 | Kiezulas | |
| 5,061,738 A | 10/1991 | Solomon et al. | |
| 5,092,841 A | 3/1992 | Spears | |
| 5,100,883 A | 3/1992 | Schiehser | |
| 5,102,402 A | 4/1992 | Dror et al. | |
| 5,102,876 A | 4/1992 | Caufield | |
| 5,118,677 A | 6/1992 | Caufield | |
| 5,118,678 A | 6/1992 | Kao et al. | |
| 5,120,322 A | 6/1992 | Davis et al. | |
| 5,120,725 A | 6/1992 | Kao et al. | |
| 5,120,726 A | 6/1992 | Failli et al. | |
| 5,120,727 A | 6/1992 | Kao et al. | |
| 5,120,842 A | 6/1992 | Failli et al. | |
| 5,130,307 A | 7/1992 | Failli et al. | |
| 5,135,516 A | 8/1992 | Sahatjian et al. | |
| 5,138,051 A | 8/1992 | Hughes et al. | |
| 5,151,413 A | 9/1992 | Caufield et al. | |
| 5,162,333 A | 11/1992 | Failli et al. | |
| 5,164,299 A | 11/1992 | Lambert | |
| 5,177,203 A | 1/1993 | Failli et al. | |
| 5,194,447 A | 3/1993 | Kao | |
| 5,196,596 A | 3/1993 | Abatjoglou | |
| 5,199,951 A | 4/1993 | Spears | |
| 5,221,670 A | 6/1993 | Caufield | |
| 5,221,740 A | 6/1993 | Hughes | |
| 5,233,036 A | 8/1993 | Hughes | |
| 5,252,579 A | 10/1993 | Skotnicki et al. | |
| 5,254,089 A | 10/1993 | Wang et al. | |
| 5,260,300 A | 11/1993 | Hu | |
| 5,262,423 A | 11/1993 | Kao | |
| 5,269,770 A | 12/1993 | Conway et al. | |
| 5,302,584 A | 4/1994 | Kao et al. | |
| 5,304,121 A | 4/1994 | Sahatjian | |
| 5,324,261 A | 6/1994 | Amundson et al. | |
| 5,346,893 A | 9/1994 | Failli et al. | |
| 5,349,060 A | 9/1994 | Kao et al. | |
| 5,362,718 A | 11/1994 | Skotnicki et al. | |
| 5,370,614 A | 12/1994 | Amundson et al. | |
| 5,373,014 A | 12/1994 | Failli et al. | |
| 5,378,696 A | 1/1995 | Caufield | |
| 5,378,836 A | 1/1995 | Kao et al. | |
| 5,380,298 A | 1/1995 | Zabetakis et al. | |
| 5,380,299 A | 1/1995 | Fearnot et al. | |
| 5,385,908 A | 1/1995 | Nelson et al. | |
| 5,385,909 A | 1/1995 | Nelson et al. | |
| 5,385,910 A | 1/1995 | Ocain et al. | |
| 5,387,680 A | 2/1995 | Nelson | |
| 5,389,639 A | 2/1995 | Failli et al. | |
| 5,391,730 A | 2/1995 | Skotnicki et al. | |
| 5,411,967 A | 5/1995 | Kao et al. | |
| 5,441,759 A | 8/1995 | Crouther et al. | |
| 5,446,048 A | 8/1995 | Failli et al. | |
| 5,463,048 A | 10/1995 | Skotnicki et al. | |
| 5,464,650 A | 11/1995 | Berg et al. | |
| 5,480,988 A | 1/1996 | Failli et al. | |
| 5,480,989 A | 1/1996 | Kao et al. | |
| 5,482,945 A | 1/1996 | Armstrong et al. | |
| 5,489,680 A | 2/1996 | Failli et al. | |
| 5,490,839 A | 2/1996 | Wang et al. | |
| 5,491,231 A | 2/1996 | Nelson et al. | |
| 5,496,276 A | 3/1996 | Wang et al. | |
| 5,504,091 A | 4/1996 | Molnar-Kimber et al. | |
| 5,504,204 A | 4/1996 | Failli et al. | |
| 5,508,399 A | 4/1996 | Kao et al. | |
| 5,509,899 A | 4/1996 | Fan et al. | |
| 5,516,781 A | 5/1996 | Morris et al. | |
| 5,525,348 A | 6/1996 | Whitbourne et al. | |
| 5,525,610 A | 6/1996 | Caufield et al. | |
| 5,530,007 A | 6/1996 | Kao et al. | |
| 5,530,121 A | 6/1996 | Kao et al. | |
| 5,532,355 A | 7/1996 | Skotnicki et al. | |
| 5,536,729 A | 7/1996 | Waranis et al. | |
| 5,559,121 A | 9/1996 | Harrison et al. | |
| 5,559,227 A | 9/1996 | Failli et al. | |
| 5,563,145 A | 10/1996 | Failli et al. | |
| 5,563,146 A | 10/1996 | Morris | |
| 5,567,709 A | 10/1996 | Skotnicki et al. | |
| 5,573,518 A | 11/1996 | Haaga | |
| 5,599,307 A | 2/1997 | Bacher et al. | |
| 5,607,463 A | 3/1997 | Schwartz et al. | |
| 5,609,629 A | 3/1997 | Fearnot et al. | |
| 5,632,772 A | 5/1997 | Alcime et al. | |
| 5,674,192 A | 10/1997 | Sahatjian et al. | |
| 5,674,287 A | 10/1997 | Slepian et al. | |
| 5,679,400 A | 10/1997 | Tuch | |
| 5,693,034 A | 12/1997 | Buscemi et al. | |
| 5,716,981 A | 2/1998 | Hunter et al. | |
| 5,733,925 A | 3/1998 | Kunz et al. | |
| 5,738,901 A | 4/1998 | Wang et al. | |
| 5,752,930 A | 5/1998 | Rise et al. | |
| 5,766,158 A | 6/1998 | Opolski | |
| 5,776,184 A | 7/1998 | Tuch | |
| 5,776,943 A | 7/1998 | Christians et al. | |
| 5,780,462 A | 7/1998 | Lee et al. | |
| 5,797,887 A | 8/1998 | Rosen et al. | |
| 5,807,306 A | 9/1998 | Shapland et al. | |
| 5,824,049 A | 10/1998 | Ragheb et al. | |
| 5,827,289 A | 10/1998 | Reiley et al. | |
| 5,843,089 A | 12/1998 | Sahatjian et al. | |
| 5,865,814 A | 2/1999 | Tuch | |
| 5,868,719 A | 2/1999 | Tsukernik | |
| 5,873,904 A | 2/1999 | Ragheb et al. | |
| 5,879,697 A | 3/1999 | Ding et al. | |
| 5,893,840 A | 4/1999 | Hull et al. | |
| 5,919,145 A | 7/1999 | Sahatjian | |
| 5,919,570 A | 7/1999 | Hostettler et al. | |
| 5,922,730 A | 7/1999 | Hu et al. | |
| 5,947,977 A | 9/1999 | Slepian et al. | |
| 5,954,706 A | 9/1999 | Sahatjian | |
| 5,977,163 A | 11/1999 | Li | |
| 5,981,568 A | 11/1999 | Kunz et al. | |
| 5,985,325 A | 11/1999 | Nagi | |
| 5,989,591 A | 11/1999 | Nagi | |
| 6,015,809 A | 1/2000 | Zhu et al. | |
| 6,042,875 A | 3/2000 | Ding et al. | |
| 6,050,980 A | 4/2000 | Wilson | |
| 6,056,722 A | 5/2000 | Jayaraman | |
| 6,074,659 A | 6/2000 | Kunz et al. | |
| 6,096,070 A | 8/2000 | Ragheb et al. | |
| 6,120,904 A | 9/2000 | Hostettler et al. | |
| 6,129,705 A | 10/2000 | Grantz | |
| 6,146,358 A | 11/2000 | Rowe | |
| 6,176,849 B1 | 1/2001 | Yang et al. | |
| 6,218,016 B1 | 4/2001 | Tedeschi et al. | |
| 6,221,467 B1 | 4/2001 | Nazarova et al. | |
| 6,228,393 B1 | 5/2001 | DiCosmo et al. | |
| 6,248,363 B1 | 6/2001 | Patel et al. | |
| 6,261,630 B1 | 7/2001 | Nazarova et al. | |
| 6,280,411 B1 | 8/2001 | Lennox | |
| 6,294,192 B1 | 9/2001 | Patel et al. | |
| 6,299,604 B1 | 10/2001 | Ragheb et al. | |
| 6,299,980 B1 | 10/2001 | Shah et al. | |
| 6,306,144 B1 | 10/2001 | Sydney et al. | |
| 6,306,166 B1 | 10/2001 | Barry et al. | |
| 6,312,406 B1 | 11/2001 | Jayaraman | |
| 6,328,970 B1 | 12/2001 | Molnar-Kimber et al. | |
| 6,331,547 B1 | 12/2001 | Zhu et al. | |
| 6,335,029 B1 | 1/2002 | Kamath et al. | |
| 6,364,856 B1 | 4/2002 | Ding et al. | |
| 6,364,893 B1 | 4/2002 | Sahatjian et al. | |
| 6,395,326 B1 | 5/2002 | Castro et al. | |
| 6,409,716 B1 | 6/2002 | Sahatjian et al. | |
| 6,419,692 B1 | 7/2002 | Yang et al. | |
| 6,432,973 B1 | 8/2002 | Zhu et al. | |
| 6,443,941 B1 | 9/2002 | Slepian et al. | |
| 6,444,324 B1 | 9/2002 | Yang et al. | |
| 6,458,138 B1 | 10/2002 | Sydney et al. | |
| 6,506,408 B1 | 1/2003 | Palasis | |
| 6,524,274 B1 | 2/2003 | Rosenthal et al. | |
| 6,528,150 B2 | 3/2003 | Nazarova et al. | |
| 6,544,544 B2 | 4/2003 | Hunter et al. | |
| 6,571,125 B2 | 5/2003 | Thompson | |
| 6,589,215 B2 | 7/2003 | Yang et al. | |
| 6,589,546 B2 | 7/2003 | Kamath et al. | |
| 6,592,548 B2 | 7/2003 | Jayaraman | |

| Patent/Pub No. | Date | Inventor |
|---|---|---|
| 6,610,035 B2 | 8/2003 | Yang et al. |
| 6,616,650 B1 | 9/2003 | Rowe |
| 6,656,156 B2 | 12/2003 | Yang et al. |
| 6,677,357 B2 | 1/2004 | Zhu et al. |
| 6,680,330 B2 | 1/2004 | Zhu et al. |
| 6,682,545 B1 | 1/2004 | Kester |
| 6,699,272 B2 | 3/2004 | Slepian et al. |
| 6,730,064 B2 | 5/2004 | Ragheb et al. |
| 6,774,278 B1 | 8/2004 | Ragheb et al. |
| 6,890,339 B2 | 5/2005 | Sahatjian et al. |
| 6,890,546 B2 | 5/2005 | Mollison et al. |
| 6,893,431 B2 | 5/2005 | Naimark et al. |
| 6,899,731 B2 | 5/2005 | Li et al. |
| 6,918,869 B2 | 7/2005 | Shaw et al. |
| 6,921,390 B2 | 7/2005 | Bucay-Couto et al. |
| 6,939,320 B2 | 9/2005 | Lennox |
| 6,958,153 B1 | 10/2005 | Ormerod et al. |
| 6,991,809 B2 | 1/2006 | Anderson |
| 6,997,949 B2 | 2/2006 | Tuch |
| 7,008,411 B1 | 3/2006 | Mandrusov et al. |
| 7,025,752 B2 | 4/2006 | Rice et al. |
| 7,048,714 B2 | 5/2006 | Richter |
| 7,056,550 B2 | 6/2006 | Davila et al. |
| 7,060,051 B2 | 6/2006 | Palasis |
| 7,066,904 B2 | 6/2006 | Rosenthal et al. |
| 7,077,859 B2 | 7/2006 | Sirhan et al. |
| 7,108,684 B2 | 9/2006 | Farnan |
| 7,144,419 B2 | 12/2006 | Cheng et al. |
| 7,153,957 B2 | 12/2006 | Chew et al. |
| 7,160,317 B2 | 1/2007 | McHale et al. |
| 7,163,555 B2 | 1/2007 | Dinh |
| 7,172,619 B2 | 2/2007 | Richter |
| 7,175,873 B1 | 2/2007 | Roorda et al. |
| 7,176,261 B2 | 2/2007 | Tijsma et al. |
| 7,179,251 B2 | 2/2007 | Palasis |
| 7,198,637 B2 | 4/2007 | Deshmukh et al. |
| 7,208,009 B2 | 4/2007 | Richter |
| 7,214,198 B2 | 5/2007 | Greco et al. |
| 7,226,586 B2 | 6/2007 | Fitzhugh et al. |
| 7,232,573 B1 | 6/2007 | Ding |
| 7,235,096 B1 | 6/2007 | Van Tassel et al. |
| 7,244,444 B2 | 7/2007 | Bates |
| 7,247,313 B2 | 7/2007 | Roorda et al. |
| 7,282,213 B2 | 10/2007 | Schroeder et al. |
| 7,285,304 B1 | 10/2007 | Hossainy et al. |
| 7,292,885 B2 | 11/2007 | Scott et al. |
| 7,294,329 B1 | 11/2007 | Ding |
| 7,306,580 B2 | 12/2007 | Paul et al. |
| 2001/0002435 A1 | 5/2001 | Berg et al. |
| 2001/0018072 A1 | 8/2001 | Unger |
| 2001/0034363 A1 | 10/2001 | Li et al. |
| 2002/0010419 A1 | 1/2002 | Jayaraman |
| 2002/0039594 A1 | 4/2002 | Unger |
| 2002/0077684 A1 | 6/2002 | Clemens et al. |
| 2002/0082552 A1 | 6/2002 | Ding et al. |
| 2002/0095114 A1 | 7/2002 | Palasis |
| 2002/0098278 A1 | 7/2002 | Bates |
| 2002/0099332 A1 | 7/2002 | Slepian et al. |
| 2002/0102280 A1 | 8/2002 | Anderson |
| 2002/0138048 A1 | 9/2002 | Tuch |
| 2002/0151844 A1 | 10/2002 | Yang et al. |
| 2002/0183380 A1 | 12/2002 | Hunter |
| 2002/0192280 A1 | 12/2002 | Hunter |
| 2003/0004209 A1 | 1/2003 | Hunter et al. |
| 2003/0045587 A1 | 3/2003 | Anderson |
| 2003/0064965 A1 | 4/2003 | Richter |
| 2003/0100577 A1 | 5/2003 | Zhu et al. |
| 2003/0100886 A1 | 5/2003 | Segal et al. |
| 2003/0100887 A1 | 5/2003 | Scott et al. |
| 2003/0114477 A1 | 6/2003 | Zhu et al. |
| 2003/0114791 A1 | 6/2003 | Rosenthal et al. |
| 2003/0157032 A1 | 8/2003 | Cavaillon et al. |
| 2003/0157161 A1 | 8/2003 | Hunter |
| 2003/0207936 A1 | 11/2003 | Chen |
| 2003/0216699 A1 | 11/2003 | Falotico |
| 2003/0235602 A1 | 12/2003 | Schwarz |
| 2004/0018296 A1 | 1/2004 | Castro et al. |
| 2004/0037886 A1 | 2/2004 | Hsu |
| 2004/0062810 A1 | 4/2004 | Hunter |
| 2004/0073284 A1 | 4/2004 | Bates et al. |
| 2004/0076672 A1 | 4/2004 | Hunter |
| 2004/0077677 A1 | 4/2004 | Ashraf et al. |
| 2004/0087902 A1 | 5/2004 | Richter |
| 2004/0127551 A1 | 7/2004 | Zhang et al. |
| 2004/0156816 A1 | 8/2004 | Anderson |
| 2004/0167152 A1 | 8/2004 | Rubino et al. |
| 2004/0176339 A1 | 9/2004 | Sherman et al. |
| 2004/0197408 A1 | 10/2004 | Gravett |
| 2004/0201117 A1 | 10/2004 | Anderson |
| 2004/0202712 A1 | 10/2004 | Lambert et al. |
| 2004/0219214 A1 | 11/2004 | Gravett |
| 2004/0224003 A1 | 11/2004 | Schultz |
| 2004/0225077 A1 | 11/2004 | Gravett |
| 2004/0230176 A1 | 11/2004 | Shanahan et al. |
| 2004/0258662 A1 | 12/2004 | Gibbons, Jr. et al. |
| 2005/0025802 A1 | 2/2005 | Richard et al. |
| 2005/0038409 A1 | 2/2005 | Segal et al. |
| 2005/0042268 A1 | 2/2005 | Aschkenasy et al. |
| 2005/0049271 A1 | 3/2005 | Benjamin et al. |
| 2005/0054978 A1 | 3/2005 | Segal et al. |
| 2005/0055078 A1 | 3/2005 | Campbell |
| 2005/0080477 A1 | 4/2005 | Sydney et al. |
| 2005/0101522 A1 | 5/2005 | Speck et al. |
| 2005/0123582 A1 | 6/2005 | Sung et al. |
| 2005/0152983 A1 | 7/2005 | Ashraf et al. |
| 2005/0159704 A1 | 7/2005 | Scott et al. |
| 2005/0182361 A1 | 8/2005 | Lennox |
| 2005/0186244 A1 | 8/2005 | Hunter et al. |
| 2005/0191323 A1 | 9/2005 | Chen |
| 2005/0191333 A1 | 9/2005 | Hsu |
| 2005/0209664 A1 | 9/2005 | Hunter et al. |
| 2005/0222191 A1 | 10/2005 | Falotico et al. |
| 2005/0234086 A1 | 10/2005 | Gu et al. |
| 2005/0234087 A1 | 10/2005 | Gu et al. |
| 2005/0234234 A1 | 10/2005 | Gu et al. |
| 2005/0238584 A1 | 10/2005 | Annapragada et al. |
| 2005/0239178 A1 | 10/2005 | Ruppen et al. |
| 2005/0250672 A9 | 11/2005 | Speck et al. |
| 2005/0251249 A1 | 11/2005 | Sahatjian et al. |
| 2005/0256564 A1 | 11/2005 | Yang et al. |
| 2005/0272758 A1 | 12/2005 | Bayever et al. |
| 2006/0020243 A1 | 1/2006 | Speck et al. |
| 2006/0040971 A1 | 2/2006 | Zhu et al. |
| 2006/0051392 A1 | 3/2006 | Heruth et al. |
| 2006/0052744 A1 | 3/2006 | Weber |
| 2006/0067977 A1 | 3/2006 | Labrecque et al. |
| 2006/0094745 A1 | 5/2006 | Ruffalo, Jr. |
| 2006/0112536 A1 | 6/2006 | Herweck et al. |
| 2006/0121117 A1 | 6/2006 | Hunter |
| 2006/0121545 A1 | 6/2006 | Molnar-Kimber et al. |
| 2006/0127445 A1 | 6/2006 | Hunter |
| 2006/0135549 A1 | 6/2006 | Graziani et al. |
| 2006/0135550 A1 | 6/2006 | Graziani et al. |
| 2006/0165753 A1 | 7/2006 | Richard |
| 2006/0183766 A1 | 8/2006 | Boni et al. |
| 2006/0184236 A1 | 8/2006 | Jones et al. |
| 2006/0188543 A1 | 8/2006 | Feng |
| 2006/0199834 A1 | 9/2006 | Zhu |
| 2006/0199954 A1 | 9/2006 | Shaw et al. |
| 2006/0224237 A1 | 10/2006 | Furst et al. |
| 2006/0230476 A1 | 10/2006 | Atanasoka et al. |
| 2006/0240113 A1 | 10/2006 | Hunter |
| 2006/0257444 A1 | 11/2006 | Tropsha et al. |
| 2006/0257445 A1 | 11/2006 | Tropsha et al. |
| 2006/0282114 A1 | 12/2006 | Barone |
| 2007/0003629 A1 | 1/2007 | Hunter |
| 2007/0003630 A1 | 1/2007 | Hunter |
| 2007/0020308 A1 | 1/2007 | Richard et al. |
| 2007/0020380 A1 | 1/2007 | Ding |
| 2007/0032694 A1 | 2/2007 | Dinkelborg et al. |
| 2007/0050010 A1 | 3/2007 | Bates et al. |
| 2007/0059434 A1 | 3/2007 | Roorda et al. |
| 2007/0065484 A1 | 3/2007 | Chudzik et al. |
| 2007/0073385 A1 | 3/2007 | Schaeffer et al. |
| 2007/0077347 A1 | 4/2007 | Richter |
| 2007/0078446 A1 | 4/2007 | Lavelle |
| 2007/0117925 A1 | 5/2007 | Strickler et al. |
| 2007/0128118 A1 | 6/2007 | Yu et al. |

| | | | |
|---|---|---|---|
| 2007/0142772 A1 | 6/2007 | Deshmukh et al. |
| 2007/0142905 A1 | 6/2007 | Hezi-Yamit et al. |
| 2007/0150043 A1 | 6/2007 | Richter |
| 2007/0150047 A1 | 6/2007 | Ruane et al. |
| 2007/0161967 A1 | 7/2007 | Fischer, Jr. et al. |
| 2007/0162103 A1 | 7/2007 | Case et al. |
| 2007/0167735 A1 | 7/2007 | Zhong et al. |
| 2007/0168012 A1 | 7/2007 | Ragheb et al. |
| 2007/0184083 A1 | 8/2007 | Coughlin |
| 2007/0191934 A1 | 8/2007 | Blakstvedt et al. |
| 2007/0198080 A1 | 8/2007 | Ding et al. |
| 2007/0212394 A1 | 9/2007 | Reyes et al. |
| 2007/0218246 A1 | 9/2007 | Ding |
| 2007/0219642 A1 | 9/2007 | Richter |
| 2007/0225799 A1 | 9/2007 | Doty |
| 2007/0237803 A1 | 10/2007 | Cheng et al. |
| 2007/0244284 A1 | 10/2007 | Cheng et al. |
| 2007/0244548 A1 | 10/2007 | Myers et al. |
| 2007/0264307 A1 | 11/2007 | Chen et al. |
| 2007/0265565 A1 | 11/2007 | Johnson |
| 2007/0276466 A1 | 11/2007 | Lavelle et al. |
| 2007/0282422 A1 | 12/2007 | Biggs et al. |
| 2007/0298069 A1 | 12/2007 | Bucay-Couto et al. |
| 2008/0038307 A1 | 2/2008 | Hoffmann |
| 2008/0082552 A1 | 4/2008 | Krishnaswamy |
| 2008/0102033 A1 | 5/2008 | Speck et al. |
| 2008/0102034 A1 | 5/2008 | Speck et al. |
| 2008/0114331 A1 | 5/2008 | Holman et al. |
| 2008/0215137 A1 | 9/2008 | Epstein et al. |
| 2008/0274159 A1 | 11/2008 | Shultz |
| 2008/0274266 A1 | 11/2008 | Davis et al. |
| 2009/0010987 A1 | 1/2009 | Parker et al. |
| 2009/0324682 A1 | 12/2009 | Popowski |
| 2010/0030183 A1 | 2/2010 | Toner et al. |
| 2010/0068238 A1 | 3/2010 | Managoli et al. |
| 2010/0179475 A1 | 7/2010 | Hoffman et al. |
| 2010/0272773 A1 | 10/2010 | Kangas et al. |
| 2010/0324645 A1 | 12/2010 | Stankus et al. |

FOREIGN PATENT DOCUMENTS

| | | |
|---|---|---|
| EP | 0 702 557 A1 | 3/1996 |
| EP | 0 706 376 B2 | 4/1996 |
| EP | 0 711 158 A1 | 5/1996 |
| EP | 0 879 595 A2 | 11/1998 |
| EP | 1 118 325 A2 | 7/2001 |
| EP | 1 372 737 A2 | 1/2004 |
| EP | 1 468 660 A2 | 10/2004 |
| EP | 1 510 220 A1 | 3/2005 |
| EP | 1 539 266 A1 | 6/2005 |
| EP | 1 539 267 | 6/2005 |
| EP | 1 576 970 A1 | 9/2005 |
| EP | 1 586 338 A2 | 10/2005 |
| EP | 1 649 853 | 4/2006 |
| EP | 1 666 070 A1 | 6/2006 |
| EP | 1 666 071 B1 | 6/2006 |
| EP | 1 669 092 A1 | 6/2006 |
| EP | 1 857 127 | 11/2007 |
| EP | 1 913 962 A1 | 4/2008 |
| EP | 1 970 185 | 9/2008 |
| EP | 2 127 617 | 12/2009 |
| WO | WO 92/11890 A1 | 7/1992 |
| WO | WO 94/07484 | 4/1994 |
| WO | WO 94/07529 | 4/1994 |
| WO | WO 94/16706 | 8/1994 |
| WO | WO 94/26291 | 11/1994 |
| WO | WO 95/03036 | 2/1995 |
| WO | WO 95/03795 | 2/1995 |
| WO | WO 96/25176 | 8/1996 |
| WO | WO 96/39949 | 12/1996 |
| WO | WO 97/25977 | 7/1997 |
| WO | WO 98/02114 | 1/1998 |
| WO | WO 98/14174 | 4/1998 |
| WO | WO 98/30249 | 7/1998 |
| WO | WO 98/36784 | 8/1998 |
| WO | WO 98/57671 A2 | 12/1998 |
| WO | WO 99/08729 | 2/1999 |
| WO | WO 00/21584 | 4/2000 |
| WO | WO 00/32238 | 6/2000 |
| WO | WO 00/32267 | 6/2000 |
| WO | WO 00/44414 | 8/2000 |
| WO | WO 00/45744 A1 | 8/2000 |
| WO | WO 01/24866 | 4/2001 |
| WO | WO 02/076509 A2 | 10/2002 |
| WO | WO 2004/006976 | 1/2004 |
| WO | WO 2004/026357 A1 | 4/2004 |
| WO | WO 2004/028582 A2 | 4/2004 |
| WO | WO 2004/028610 | 4/2004 |
| WO | WO 2005/011769 A2 | 2/2005 |
| WO | WO 2006/023859 A1 | 3/2006 |
| WO | WO 2006/081210 A2 | 8/2006 |
| WO | WO 2006/101573 A1 | 9/2006 |
| WO | WO 2006/124647 A1 | 11/2006 |
| WO | WO 2007/047416 A2 | 4/2007 |
| WO | WO 2007/079560 A2 | 7/2007 |
| WO | WO 2007/134239 A2 | 11/2007 |
| WO | WO 2007/139931 A2 | 12/2007 |
| WO | WO 2007/149161 A2 | 12/2007 |
| WO | WO 2008/003298 A2 | 1/2008 |
| WO | WO 2008/063576 A2 | 5/2008 |
| WO | WO 2008/086794 | 7/2008 |
| WO | WO 2008/114585 | 9/2008 |

OTHER PUBLICATIONS

International Search Report for International Application No. PCT/US2008/006415, dated Nov. 24, 2008, Ex. Nora Hick.

International Search Report for International Application No. PCT/US2008/006348, dated Jan. 28, 2009, Ex. Tatjana John.

International Search Report for International Application No. PCT/US2008/006417, dated Nov. 24, 2008, Ex. Nora Hick.

International Search Report for International Application No. PCT/2008/007177, Dec. 2, 2008, Examiner Tatjana John.

International Search Report for International Application No. PCT/2007/024116, dated Nov. 20, 2008, Examiner Tatjana John.

Li J. Chiang et al., "Potent inhibition of tumor survival in vivo by β-lapachone plus taxol: Combining drugs imposes different artificial checkpoints," PNAS, vol. 96, No. 23, Nov. 9, 1999, at pp. 13369-13374.

D.M. Jackson et al., "Current usage of contract agents, anticoagulant and antiplatelet drugs in angiography and angioplasty in the UK," Department of Diagnostic Radiology, Hammersmith Hospital, London, UK, Clinical Radiology (1995), 50, pp. 699-704.

Seymour R. Halpin SF et al., "Corticosteroid prophylaxis for patients with increased risk of adverse reactions to intravascular contrast agents: a survey of current practice in the UK," Department of Radiology, University Hospital of Wales, Heath Park, Cardiff, Clinical Radiology (1994), 49, pp. 791-795.

Toshimitsu Konno, M.D., et al., "Selective targeting of anti-cancer drug and simultaneous imaging enhancement in solid tumors by arterially administered lipid contrast medium," Cancer 54:2367-2374, 1984.

Ken Iwai et al., "Use of oily contrast medium for selective drug targeting to sumor: Enhanced therapeutic effect and X-ray image," Cancer Research, 44, 2115-2121, May 1994.

Journal of Microencapsulation, 17, 6, Nov. 2, 2000, p. 789-799.

New England Journal of Medicine, 1995, 332: 1004-1014.

Chun Li, et al, "Synthesis, Biodistribution and Imaging Properties of Indium-111-DTPA-Paclitaxel in Mice Bearing Mammary Tumors," The Journal of Nuclear Medicine, vol. 38, No. 7, Jul. 1997, 1042-1047.

D. M. Long et al., "Perflurocarbon Compounds As X-Ray Contrast Media In The Lungs," Bulletin de la Societe Internationale De Chirurgie, vol. 2, 1975, 137-141.

Herdeg et al., "Paclitaxel: Ein Chemotherapeuticum zum Restenoseprophylaxe? Experimentell Untersuchungen in vitro und in vivo," Z Kardiol, vol. 89 (2000) pp. 390-397.

Prashant N. Chhajed et al., "Patterns of Pulmonary Complications Associated with Sirolimus," Respiration: International Review of Thoracic Diseases, vol. 73, No. 3, Mar. 2006, at pp. 367-374.

Laure Champion et al., "Brief Communication: Sirolimus-Associated Pneumonitis: 24 Cases in Renal Transplant Recipients," Annals of Internal Medicine, vol. 144, No. 7, Apr. 4, 2006, at pp. 505-509.

Gyula Ostoros et al., "Paclitaxel Induced Pulmonary Fibrosis," Lung Cancer, Elsevier, Amsterdam, NL, vol. 41, Aug. 1, 2003, at p. S280.

Gyula Ostoros et al., "Fatal Pulmonary Fibrosis Induced Paclitaxel: A Case Report and Review of the Literature," International Journal of Gynecological Cancer, vol. 16, Suppl. 1, Jan. 2006, at pp. 391-393.

Baumbach et al., "Local Drug Delivery: Impact of Pressure Substance Characteristics, and Stenting on Drug Transfer Into the Arterial Wall," Catheterization and Cardiovascular Interventions, vol. 47, pp. 102-106 (1999).

Charles et al., "Ceramide-Coated Balloon Catheters Limit Neointimal Hyperplasia After Stretch Injury in Carotid Arteries," Circulation Research published by the American Heart Association, 87, pp. 282-288 (2000).

English Language Abstract for EP 1 372 737 A2.

English Language Abstract for EP 1 539 266 A1.

English Language Abstract for EP 1 666 070 A1.

English Language Abstract for EP 1 666 071 A1.

English Language Abstract for EP 1 669 092 A1.

English Language Abstract for WO 02/076509.

English Language Abstract for WO 2004/028582.

English Language Abstract for WO 2004/028610.

English Language Abstract for WO 2008/003298 A2.

International Search Report for International Application No. PCT/US2009/004868, mailed Jan. 1, 2010, Ex. Maria Van der Hoeven.

International Search Report for International Application No. PCT/US2010/028599, dated Dec. 21, 2010.

Office Action in co-pending U.S. Appl. No. 12/135,648, dated Feb. 18, 2011.

Creel et al., 2000 Circulation Research. Bd. 86, S. 879-884.

English Language Abstract for DE 101 15 740, Oct. 2, 2002.

English Language Abstract for EP 1 539 267, Jun. 15, 2005.

English Language Abstract for EP 1 857 127, Nov. 21, 2007.

English Language Abstract for WO 2008/086794, Jul. 24, 2008.

J.F. Mitchel et al., "Inhibition of Platelet Deposition and Lysis of Intracoronary Thrombus During Balloon Angioplasty Using Urokinase-Coated Hydrogel Balloons." Circulation 90, (Oct. 1994), pp. 1979-1988.

J.H. Baron, et al., "In vitro evaluation of c7E3-Fab (ReoPro) eluting polymer-coated coronary stents." Cardiovascular Research, 46 (2000) pp. 585-594.

K. Kandarpa et al., "Mural Delivery of Iloprost with Use of Hydrogel-coated Balloon Catheters Suppresses Local Platelet Aggregation." J. Vasc. Interv. Radiol. 8, pp. 997-1004, Nov./Dec. 1997.

K. Kandarpa et al., "Site-specific Delivery of Iloprost during Experimental Angioplasty Suppresses Smooth Muscle Cell Proliferation." J. Vasc. Interv. Radiol. 9, pp. 487-493, (1998).

Leo, et al., (1971). "Partition coefficients and their uses." Chem Rev 71 (6):525-537.

Office Action in co-pending U.S. Appl. No. 11/942,452, dated Oct. 13, 2010.

Office Action in co-pending U.S. Appl. No. 11/942,459, dated Sep. 27, 2010.

PPD, "Evaluation of Butanol-Buffer Distribution Properties of C6-Ceraminde." PPD Project No. 7557-001, Aug. 20, 2008, pp. 1-14.

Sangster, James (1997). "Octanol-Water Partition Coefficients: Fundamentals and Physical Chemistry." vol. 2 of Wioley Series in Solution Chemistry. Chichester: John Wiley & Sons Ltd.

Yushmanov, et al., J. Colloid Interface Sci., 1997; 191(2):384-90.

METHODS AND APPARATUSES FOR COATING BALLOON CATHETERS

CROSS REFERENCE TO RELATED APPLICATIONS

This application claims the benefit of priority under 35 U.S.C. §119 of U.S. Provisional Application No. 61/092,872, filed on Aug. 29, 2008, the disclosure of which is incorporated by reference herein.

FIELD OF THE INVENTION

Embodiments of the present invention relate to methods for coating medical devices, and particularly for coating balloon catheters. Embodiments of the present invention also relate to apparatuses used for coating these medical devices.

BACKGROUND OF THE INVENTION

It has become increasingly common to treat a variety of medical conditions by introducing a drug releasing medical device into the vascular system. For example, medical devices used for the treatment of vascular diseases include drug eluting stents. There is an increasing demand for better coating methods to control the dose of therapeutic agent and to improve drug distribution and uniformity in the coatings of these medical devices.

Methods for coating a drug eluting stent (DES) have been developed in recent years. The stent is coated with a polymer into which drug is impregnated. Methods for coating drug eluting stents include dipping in, or spraying with, the coating solution or composition. The coating composition often includes a solvent, a polymer dissolved in the solvent, and a therapeutic agent dissolved or dispersed in the coating composition. The composition is then applied to the stent by spraying the composition onto the stent or by dipping the stent in the coating composition. The solvent is allowed to evaporate, leaving a coating of the polymer and therapeutic drug on the stent surfaces. These methods are useful for coating discontinuous surfaces, such as that of a stent. The surfaces outside, inside, and in between struts of the stent can be coated by these methods. In both spraying and dipping coatings, the amount of coating transferred is not precisely controlled and has to be independently quantified for dose verification. Most of the coating does not spray onto the medical device. Thus, the amount of the coating on the medical device is less than the amount of coating that is sprayed. The amount of coating on the medical device in the dipping coating depends on solvent, solution, concentration, and adhesive property of coating to medical device. The dose or load of drug coated on the stent may be controlled by weighing the stent after the coating is dried, since a stent is a small metal implant that can easily be placed on a scale. A precise balance can be used to measure the total dose of drug coated on the device. An important limitation of these methods is that the drug dose cannot be controlled if the medical devices cannot be weighed precisely, or if the weight of the coating layer is negligible relative to the weight of the device, such as a balloon catheter. A balloon catheter typically may be an assembly of long plastic tubes that weighs, for example, approximately 10 to 20 grams. The weight of the drug coating (typically 0.1 to 10 mg) is therefore well within the measurement error of the weight of the balloon catheter itself.

Non-stent based local delivery systems, such as balloon catheters, have also been effective in the treatment and prevention of restenosis. The balloon is coated with an active agent, and when the blood vessel is dilated, the balloon is pressed against the vessel wall to deliver the active agent.

The current method for drug coating of a balloon catheter is dipping or spraying. The coating layer formed by dipping or spraying is not uniform on the surface of the balloon, and the drug is not uniformly distributed in the coating layer overlying the balloon surface. Furthermore, the dose of the drug deployed on the device after dipping or spraying is not consistent and in some cases may vary from as much as 0.5 to 11 $\mu g/mm^2$, or as much as 300%, from balloon to balloon or from one region of the balloon surface to another. In the case of spray coating, large amounts of sprayed drug will not land on the surface of the balloon catheter and the amount of the drug on the balloon catheter is less than the amount of drug sprayed. In the case of dip coating, it is also very difficult to load a large amount of drug on the balloon, even with multiple dips, because drug already on the balloon may dissolve away during subsequent dips. In both situations, sections of the device that are not desirable to coat must be masked.

Thus, there is still a need to develop an improved method and apparatus for coating highly specialized medical devices. There is still a need to develop improved methods for precisely measuring and controlling the concentration or dose of drug on the surface of coated medical devices. There is a need that the amount of drug dispensed is the same as that on the surface of the medical devices, especially balloon catheters. Furthermore, there is still a need to improve the uniformity of drug distribution in the coating layer and the uniformity of the coating on the surface of the medical device.

SUMMARY OF THE INVENTION

Embodiments of the present invention relate to methods and apparatuses for drug coating the exterior surface of a medical device, for example, the inflatable portion of a balloon catheter or a medical device that has a continuous surface. In one embodiment, the amount of the drug is premetered before its dispensement. The amount of the dispensed drug from the coating apparatus is the same as or substantially the same as that on the surface of the medical device after the coating process according to embodiments of the invention. The dispensed drug is applied as a solution, dispersion, suspension, emulsion or other mixture that is dispensed in the form of a droplet or droplets or continuous flow that then flows on the surface of the medical device. The term "solution" includes a solution, dispersion, suspension, emulsion or other mixture in embodiments of the inventions. The flow of the solution or dispersion composition on the moving surface of the medical device produces a uniform coating. In contrast to dipping or spraying coating methods, during the coating process of at least certain embodiments almost no solution is lost. In certain embodiments, almost none of the solution is lost during dispensing onto the surface of the medical device, and no drug is lost while the solvent is evaporated as the coating solution flows on the surface of the medical device. Therefore, the metered drug dose is the same as or substantially the same as the dose of the drug on the surface of the medical device.

In one embodiment, the coating composition comprises a therapeutic agent, an additive, and a solvent. In another embodiment, the coating composition comprises a therapeutic agent, a polymer, and a solvent. In another embodiment, the coating composition comprises a therapeutic agent, a hydrophilic molecule, and a solvent. In another embodiment, the coating composition comprises two or more therapeutic agents, two or more additives, and/or two or more solvents. In yet another embodiment, the coating composition comprises an additive and a solvent, but no drug, for example, in a top coating layer that might be deployed using the methods of the present invention over a drug layer previously coated on a medical device.

In one embodiment, the method for preparing a substantially uniform coated medical device comprises (1) preparing a coating solution comprising a solvent, a therapeutic agent, and an additive; (2) loading a metering dispenser with the coating solution; (3) rotating the medical device about the longitudinal axis of the device and/or moving the medical device in a linear direction along the longitudinal or transverse axis of the device; (4) dispensing the coating solution from the metering dispenser onto a surface of the medical device and flowing the coating solution on the surface of the medical device while the medical device is rotating and/or linearly moving; and (5) evaporating the solvent, forming a coating layer on the surface of the medical device.

In one embodiment, steps (2), (3), (4) and (5) occur concomitantly.

In one embodiment, steps (2), (3) (4) and (5) are repeated until a therapeutically effective amount of the therapeutic agent in the coating solution is deposited on the surface of the medical device.

In one embodiment, the medical device or a portion thereof has a continuous surface.

In one embodiment, the method further comprises a step (6) drying the medical device, (7) sterilizing the medical device; and a step (8) drying the medical device after sterilization. In one embodiment, in step (7) the medical device is sterilized with ethylene oxide and in step (8), the medical device is dried under vacuum at about 5 to 45° C. for approximately 2 to 56 hours. In one embodiment, in step (8), the medical device is dried under vacuum at about 0 to 100° C. for approximately 2 to 56 hours.

In an alternative embodiment, the medical device is fixed in place and the metering dispenser dispenses the coating solution onto the surface of the medical device while the metering dispenser is rotating about the longitudinal axis of the medical device and/or moving in a linear direction along the longitudinal or transverse axis of the medical device. In another alternative embodiment, the metering dispenser dispenses the coating solution onto the surface of the medical device while each of the metering dispenser and the medical device are rotating about the longitudinal axis of the medical device and/or moving in a linear direction along the longitudinal or transverse axis of the medical device.

In one embodiment, in step (5), the solvent is evaporated while the coating solution is moving at uniform speed, forming a substantially uniform dry coating layer over the surface of the medical device.

In one embodiment, all of the metered coating solution is deployed on the device, which allows for quantifying, without need for weighing, the drug dose in the coating layer overlying the device.

In one embodiment the medical device is a balloon catheter, and the method for preparing a substantially uniform coated balloon catheter comprises (1) preparing a coating solution comprising a solvent, a therapeutic agent, and an additive; (2) loading a metering dispenser with the coating solution; (3) inflating the balloon catheter to 0 to 3 atm, and rotating the balloon catheter about the longitudinal axis of the catheter and/or moving the balloon catheter in a linear direction along the longitudinal or transverse axis of the catheter; (4) dispensing the coating solution from the metering dispenser onto a surface of the balloon catheter and flowing the coating solution on the surface of the balloon catheter while the balloon catheter is rotating and/or linearly moving; (5) evaporating the solvent, forming a coating layer on the surface of the balloon catheter; (6) folding and wrapping the balloon catheter; and (7) drying and then sterilizing the balloon catheter. In one embodiment, step (6) comprises deflating, folding, wrapping, and packaging the balloon catheter, and step (7) comprises sterilizing the packaged balloon catheter.

In one embodiment, steps (2), (3), (4), and (5) occur concomitantly.

In one embodiment, the medical device or a portion thereof has a continuous surface.

In one embodiment, the method for preparing a coated balloon catheter comprises (1) preparing a coating solution comprising a solvent, a therapeutic agent, and an additive; (2) loading a metering dispenser with the coating solution; (3) inflating the balloon catheter to 0 to 3 atm, and rotating the balloon catheter about the longitudinal axis of the catheter and/or moving the balloon catheter in a linear direction along the longitudinal or transverse axis of the catheter; (4) dispensing the coating solution from the metering dispenser onto a surface of the balloon catheter and flowing the coating solution on the surface of the balloon catheter while the balloon catheter is rotating and/or linearly moving; (5) evaporating the solvent, forming a coating layer on the balloon catheter; (6) drying, folding and wrapping the balloon catheter; and (7) sterilizing the balloon catheter. In one embodiment, the method further comprises a step (8) drying the medical device after sterilization. In one embodiment, in step (7) the balloon catheter is sterilized with ethylene oxide, and in step (8), the balloon catheter is dried under vacuum at about 0 to 100° C. for approximately 2 to 56 hours. In one embodiment, the balloon catheter is dried under vacuum at about 5 to 45° C.

In another embodiment, the method can be used to apply multiple-layer coatings on the surface of a medical device, wherein the method comprises (1) preparing a first coating solution comprising a solvent, a therapeutic agent, and an additive; (2) loading a metering dispenser with the first coating solution; (3) rotating the medical device about the longitudinal axis of the device and/or moving the medical device in a linear direction along the longitudinal or transverse axis of the device; (4) dispensing the first coating solution from the metering dispenser onto a surface of the medical device and flowing the coating solution on the surface of the medical device while the medical device is rotating and/or linearly moving; (5) evaporating the solvent, forming a substantially uniform coating layer on the surface of the medical device; and (6) repeating steps (1), (2), (3), (4) and (5) with a second coating solution, which is the same or different from the first coating solution, forming an additional coating layer on the medical device, until the desired number of layers are obtained. In one embodiment, the method further comprises (7) sterilizing the medical device and (8) drying the medical device after sterilization. In one embodiment, in step (7) the medical device is sterilized with ethylene oxide and in step (8), the medical device is dried under vacuum at about 0 to 100° C. for approximately 2 to 56 hours. In another embodiment, in step (8), the medical device is dried under vacuum at about 5 to 60° C. for approximately 1 to 120 hours.

In one embodiment, the medical device or a portion thereof has a continuous surface.

In another embodiment, the method for preparing a medical device comprises (1) preparing a coating solution comprising a solvent, a therapeutic agent, and an additive; (2) applying the coating solution to a medical device; (3) drying the coating solution, forming a coating layer; (4) sterilizing the medical device; and (5) drying the medical device after sterilization. In one embodiment, the medical device is a balloon catheter and the balloon is inflated under low pressure (0 to 3 ATM) during the drug loading and coating. In one embodiment, in step (5), the medical device is dried under vacuum at about 5 to 60° C. for approximately 1 to 120 hours. In another embodiment, in step (5), the medical device is dried under vacuum at about 0 to 100° C. for approximately 2 to 56 hours.

In one embodiment, the present invention relates to an apparatus for coating medical devices, the apparatus comprising a metering dispenser, a coating solution storage container, and an assembly for rotation of the device around its central/axial/longitudinal axis and for translational movement of the device in a linear direction back and forth along its longitudinal and/or transverse axes. In one embodiment, the assembly moves the device linearly back and forth along a rail with uniform frequency while rotating the device at uniform rotational/tangential speed. In one embodiment, the metering dispenser moves linearly back and forth along a rail with uniform frequency while as assembly is rotating the device at uniform rotational/tangential speed.

In another embodiment of the present invention, an apparatus for coating a medical device comprises: a metering dispenser; an apparatus that rotates the medical device around its longitudinal axis and moves the medical device back and forth in the direction of its longitudinal or transverse axis; a controller coordinating the dispenser and the apparatus; and a coating solution storage container. In one embodiment, the apparatus concurrently rotates the medical device around its longitudinal axis at uniform rotational or tangential speed and translocates the device back and forth at uniform frequency in a longitudinal direction. This enables evaporation of the solvent to occur while the coating solution is moving at uniform speed over the surface of the medical device, resulting in a uniform dry coating layer.

In another embodiment, the metering dispenser includes a dispensing tip. The dispensing tip typically includes a hub and a tip. The hub is connected to the metering dispenser. The tip is used to apply coating on the medical device either by contact or non-contact. The tip opening can have different shapes including, but not limited to, circular, oval, square, and rectangular. The tip can be straight or with an angle (135°, 45° or 90°) and the tip can be rigid or flexible. The tip can be tapered, non-tapered, Teflon-lined, Teflon-coated, and Teflon-lined and crimped or the tip can be a brush. The dispensing tip can be made of metals, metal alloys, and a metal with a polymer coating or lining. For example, the dispensing tip can be made of stainless steel, polyethylene, polypropylene, polyesters, polyamides, polyurethanes, PTFE, metal with a PTFE coating or lining.

In another embodiment, the dispensing tip has an opening and a flexible tail as illustrated in FIG. 3A. The flexible tip can be metal or polymer materials. The cross section of the tip can be circular, oval, square, or rectangular. The length of the tip can be from 5 mm to 30 mm. The flexible tail can thread through the tip opening of the dispensing tip or attach to the side of the tip. In embodiments of the invention, the flexible tail contacts the balloon to be coated. During dispensing, the coating flows continuously to the balloon surface without forming droplets. The rotational and traversal movements allow the flexible tail to break the surface tension between the coating and balloon and form a uniform coating on the balloon surface.

In some embodiments, the metering dispenser comprises one of a syringe, a syringe pump, a metering pipette, and an automatic metering system. In one embodiment, the automatic metering system comprises a micro linear pump module, a dispensing controller module, a dispensing tip and other accessories from IVEK Corporation. In some embodiments, the device comprises one of a balloon catheter, a perfusion balloon catheter, an infusion catheter such as a distal perforated drug infusion tube, a perforated balloon, a spaced double balloon, a porous balloon, and a weeping balloon, a cutting balloon catheter, a scoring balloon catheter, a laser catheter, an atherectomy device, a debulking catheter, a stent, a filter, a stent graft, a covered stent, a patch, a wire, and a valve. In one embodiment, the method and apparatus of the invention is useful for coating the surface of medical devices that have a continuous surface, for example, the inflatable portion of a balloon catheter, since applying the coating composition on the surface of the medical devices while the solvent is evaporating is involved. In one embodiment, the drops of coating solution move back and forth longitudinally and transversely over the surface of the medical device while the solvent evaporates, resulting in the consistent and uniform deposition of coating solution over the device surface and resulting in a uniform dry coating layer over the surface of the medical device.

Medical devices with a continuous surface include, among others, a balloon catheter, a perfusion balloon catheter, an infusion catheter such as a distal perforated drug infusion tube, a perforated balloon, a porous balloon, and a weeping balloon, a cutting balloon catheter, a scoring balloon catheter, a stent graft, a covered stent, a patch, a wire, and leads for pacing, sensing, and defibrillation.

In one embodiment, the coating composition comprises a therapeutic agent and an additive, wherein the additive is at least one of a surfactant, a polymer, and a chemical compound (MW<1300). In embodiments of the invention, the chemical compound has one or more hydroxyl, amino, carbonyl, carboxyl, acid, amide or ester groups. In some embodiments, the chemical compound is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In embodiments of the invention, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters and derivatives thereof.

In embodiments of the invention, the additive is chosen from p-isononylphenoxypolyglycidol, PEG laurate, PEG oleate, PEG stearate, PEG glyceryl laurate, Tween 20, Tween 40, Tween 60, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerols, multiglycerols, galactitol, di(ethylene glycol), tri(ethylene glycol), tetra(ethylene glycol), penta(ethylene glycol), poly(ethylene glycol) oligomers, di(propylene glycol), tri (propylene glycol), tetra(propylene glycol, and penta(propylene glycol), poly(propylene glycol) oligomers, and derivatives and combinations thereof.

In embodiments of the invention, the polymer is one of polyolefins, polyisobutylene, ethylene-α-olefin copolymers, acrylic polymers and copolymers, polyvinyl chloride, polyvinyl methyl ether, polyvinylidene fluoride and polyvinylidene chloride, polyacrylonitrile, polyvinyl ketones, polystyrene, polyvinyl acetate, ethylene-methyl methacrylate copolymers, acrylonitrile-styrene copolymers, ABS resins, Nylon 12 and its block copolymers, polycaprolactone, polyoxymethylenes, polyesters, polyethers, polyamides, epoxy resins, polyurethanes, rayon-triacetate, cellulose, cellulose acetate, cellulose butyrate, cellophane, cellulose nitrate, cellulose propionate, cellulose ethers, carboxymethyl cellulose, chitins, polylactic acid, polyglycolic acid, polylactic acid-polyethylene oxide copolymers, polyethylene glycol, polypropylene glycol, polyvinyl alcohol, and mixtures and block copolymers thereof.

In embodiments of the invention, the therapeutic agent is one of paclitaxel and analogues thereof, rapamycin and analogues thereof, beta-lapachone and analogues thereof, biological vitamin D and analogues thereof, and a mixture of these therapeutic agents. In another embodiment, the therapeutic agent is in combination with a second therapeutic agent, wherein the therapeutic agent is one of paclitaxel, rapamycin, and analogues thereof, and wherein the second therapeutic agent is one of beta-lapachone, biological active vitamin D, and their analogues.

In embodiments of the invention, the solvent is one of water, methanol, ethanol, isopropanol, acetone, dimethylformide, tetrahydrofuran, methylethyl ketone, dimethylsulfoxide, acetonitrile, ethyl acetate, and chloroform and mixtures of these solvents.

In one embodiment, the concentration of the therapeutic agent in the coating layer is from about 1 to about 20 $\mu g/mm^2$. In one embodiment, the thickness of the coating is from about 1 to about 50 μm. In another embodiment, the thickness of the coating layer is from about 6 to about 20 μm, for example from about 8 to about 15 μm.

In one embodiment comprising a balloon catheter, the balloon diameter is in the range of about 1.0 mm to about 40 mm. In another embodiment of the PTCA balloon catheters, the balloon diameter is in the range of from about 1.0 mm to about 5.0 mm in 0.25 mm increments. In another embodiment of PTA balloon catheters, the balloon diameter is in the range of from about 2.0 mm to about 12.0 mm. In one embodiment of non-vascular balloon catheters, the balloon diameter is in the range of from about 2.0 mm to about 40 mm.

In one embodiment of balloon catheters, the balloon length is in the range of from about 5.0 mm to about 300 mm. In another embodiment of the PTCA balloon catheters, the balloon length is in the range of from about 8.0 mm to about 40.0 mm. In another embodiment of PTA balloon catheters, the balloon length is in the range of from about 8.0 mm to about 300.0 mm. In one embodiment of non-vascular balloon catheters (for example, gastric and respiratory applications), the balloon length is in the range of from about 10.0 mm to about 200 mm. In one embodiment, the balloon catheter includes a 0.014-inch, 0.018-inch, and 0.035-inch wire compatible lumen.

It is understood that both the foregoing general description and the following detailed description are exemplary and explanatory only and are not restrictive of the present invention as claimed.

DETAILED DESCRIPTION OF EXEMPLARY EMBODIMENTS

Embodiments of the present invention relate to methods and apparatuses for coating medical devices, including balloon catheters and other medical devices with continuous surfaces. A method according to embodiments of the present invention does not require weighing the medical devices after coating to control the concentration or dose of the drug on the surface of the devices. An object of embodiments of the present invention is to control the dose of the drug by using a premetering dispenser system. The uniformity of coating of the medical device is improved by applying and flowing the fluid of the coating composition on the surface of the medical device in both longitudinal and transverse directions. The coating solution of the present invention refers to the liquid drug coating composition and includes a solution, dispersion, suspension, emulsion or other mixture that is dispensed in the form of a droplet or droplets or continuous flow that then flows on the surface of the medical device. In certain embodiments, almost none of the coating solution is lost as the solution is dispensed onto the surface of the medical device, and no drug is lost while the solvent is evaporated. In these embodiments, since the coating solution is applied over the entire surface of the device (or portion thereof being coated) at a uniform speed multiple times as the solvent slowly evaporates, a uniform dried coating is deployed and remains on the device after the solvent is evaporated. Furthermore, in contrast to spraying or dipping coating methods, the metered drug dose dispensed on the surface is substantially the same as the dose of the drug on the surface of the medical device. The excellent precision of the methods of embodiments of the present invention facilitates easy calibration of pipette or meter volume to adjust for measurement errors during solution preparation.

Figure 1:
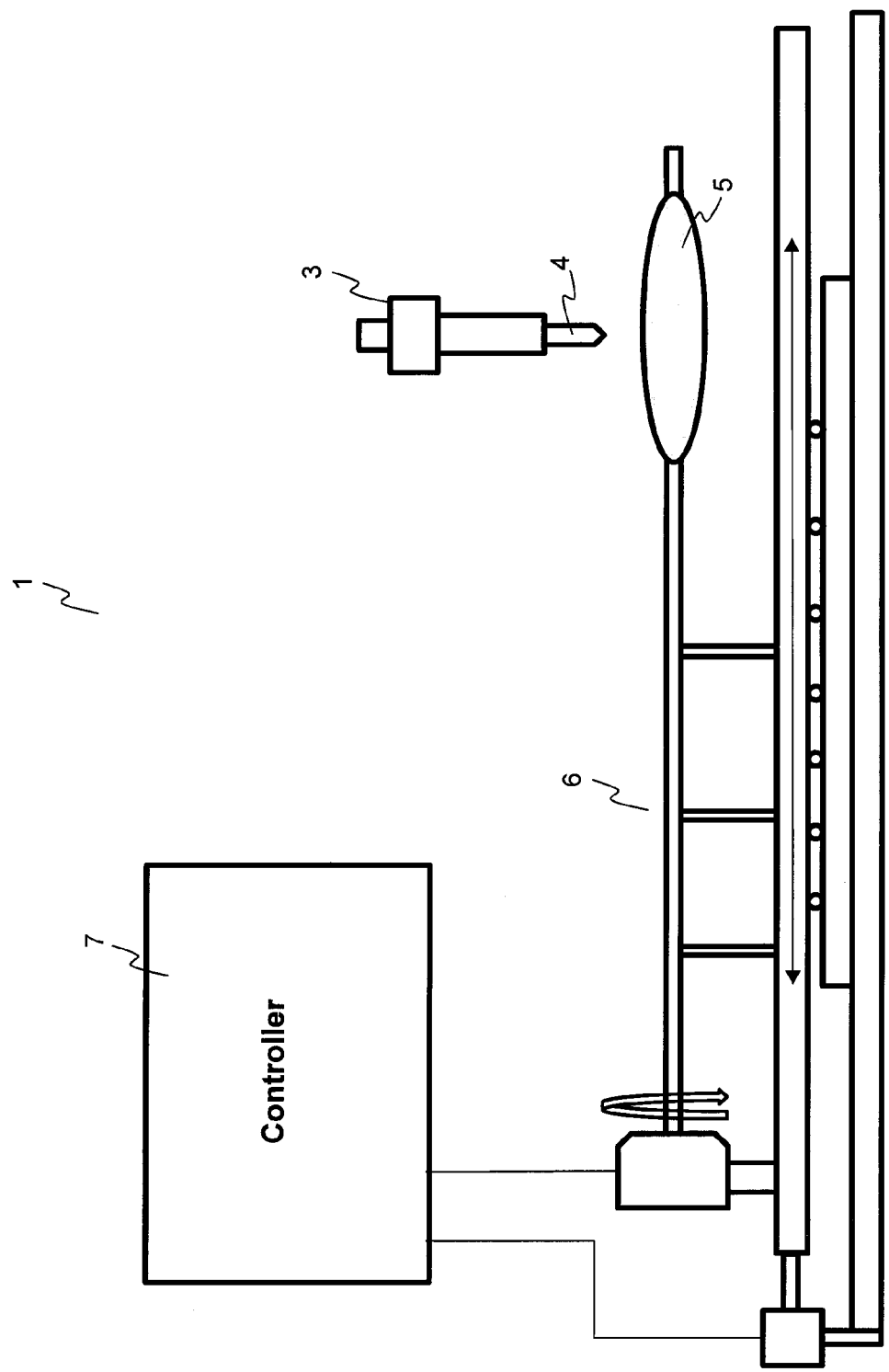
FIG. 1 is a perspective view of an exemplary embodiment of an apparatus according to embodiments of the present invention.

As shown in FIG. 1, in one embodiment, the apparatus is a semi-manual coating apparatus. The coating apparatus 1 comprises a metering dispenser 3, a dispenser tip 4, a medical device 5, and an assembly 6 for rotation (around the longitudinal axis of the device) and translation in a linear direction (back and forth in direction of the longitudinal or transverse axis of the device). In FIG. 1, the metering dispenser is a syringe or a pipette. A dispensing tip is connected to the metering dispenser for easy coating application. In FIG. 1, the medical device is a balloon catheter (only the distal end of the balloon catheter is shown). Typically, only the inflatable surface of the balloon is coated. The balloon catheter may be any suitable catheter for the desired use, including conventional balloon catheters known to one of ordinary skill in the art. The balloon catheter may be a rapid exchange or over-the-wire catheter. The balloon catheter 5 is fixed on the assembly 6 which rotates the balloon catheter and moves it back and forth linearly in the longitudinal and/or transverse directions.

Figure 2:
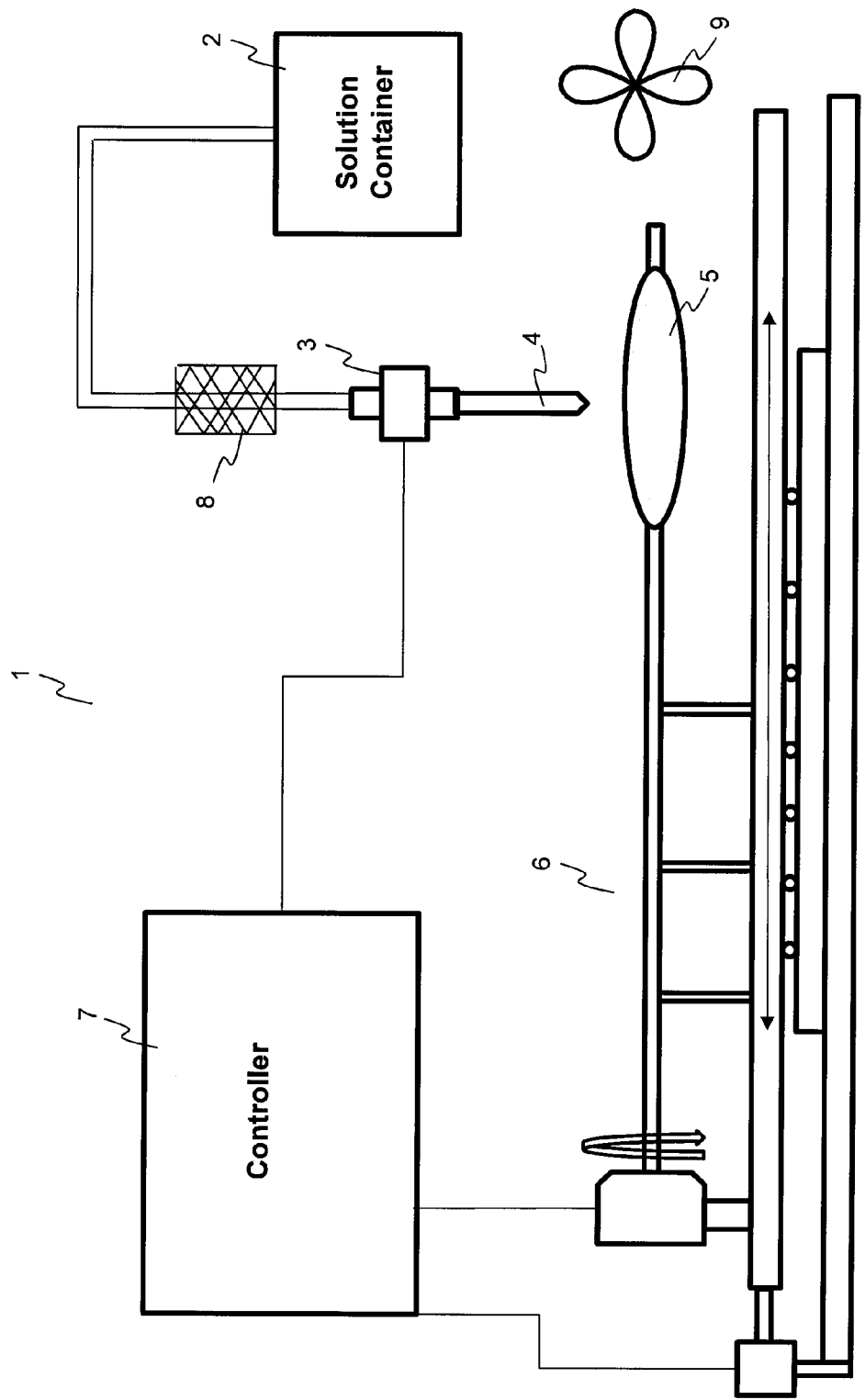
FIG. 2 is a perspective view of an exemplary embodiment of an apparatus with an automatic dispensing system according to embodiments of the present invention.

As shown in FIG. 2, in another embodiment, the apparatus is an automated coating apparatus. The coating apparatus 1 comprises a coating solution storage container 2, a filter 8, a metering dispenser 3, a dispenser tip 4, a fan 9 for accelerating solvent evaporation, a controller 7, for example a computer, a medical device 5, and an assembly 6 for rotation and translation in a linear direction. In FIG. 2, the metering dispenser is a ceramic micro linear pump (such as micro linear pump module from IVEK Corporation). The controller is a computer or a digital controller (such as Digispense 2000 controller module, a single channel dispensing systems from IVEK Corporation). The medical device is a balloon catheter in FIG. 2 (only the distal end of the balloon catheter is shown). The balloon catheter may be any suitable catheter for the desired use, including conventional balloon catheters known to one of ordinary skill in the art. The balloon catheter may be a rapid exchange or over-the-wire catheter. The storage container 2 is connected to the metering dispenser 3 via a filter 8. The balloon catheter 5 is fixed on the assembly 6 which rotates the balloon around its longitudinal axis and translocates the balloon catheter 6 linearly in longitudinal and transverse directions.

Figure 3A:
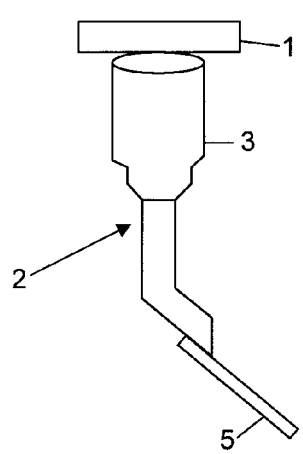
FIGS. 3A to 3E are perspective views of an exemplary embodiment of a dispensing tip according to embodiments of the present invention.
Figure 3B:
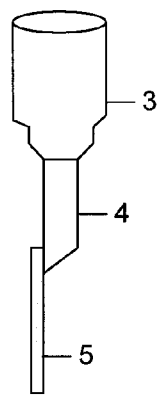
Figure 3C:
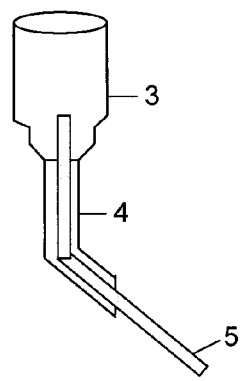
Figure 3D:
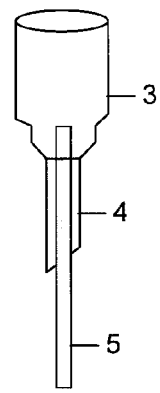
Figure 3E:
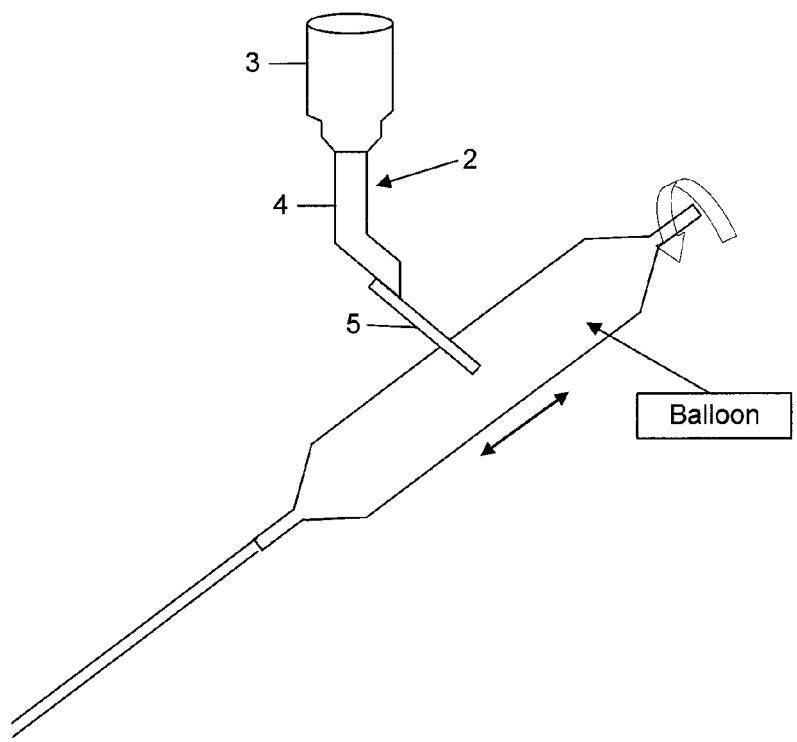

As shown in FIG. 3A, in one embodiment the metering dispenser 1 is connected to a dispensing tip 2. The dispensing tip 2 typically includes a hub 3 and a tip 4. The hub 3 is connected to the metering dispenser. The tip is used to apply coating on the medical device either by contact or non-contact. The tip opening can have different shapes including, but not limited to, circular, oval, square, and rectangular. The tip can be straight or with an angle (e.g., 135°, 45° or 90°) and the tip can be rigid or flexible. In one embodiment, the dispensing tip has a hub 3, a tip 4, and a flexible tail 5. The flexible tail 5 can thread through the tip of the dispensing tip or attach to the side of the tip as shown in FIGS. 3A, 3B, 3C, and 3D.

The coating solution or composition, according to embodiments, is prepared by mixing a fixed amount of a therapeutic agent, an additive and a solvent. The mixture is then stirred at room temperature or slight heating less than 60° C. until a homogenous solution is obtained. The solution is then filtered through a 0.45 micron filter. The metering dispenser (such as a syringe or a pipette) is used to apply a premetered coating solution in the form of droplets onto the surface of balloon catheter while the balloon catheter is rotating on its longitudinal (axial) axis and moving back and forth linearly in a longitudinal or transverse direction. The coating uniformity is obtained by applying a continuous flow or droplets of a coating solution or composition and flowing the solution or composition onto the surface of the balloon while the solvent is evaporating. The balloon is folded after the coating is solidified. The dried and folded balloon catheter is then rewrapped. The right sized balloon protector is then put on the wrapped balloon. The balloon catheter is packaged. The balloon catheter is then sterilized with ethylene oxide, E-beam or other methods. The balloon catheter is then ready for animal testing or human trials or for treating diseases such as coronary or peripheral artery stenosis.

In some embodiments, the coating properties of the coating layer are further improved by drying after sterilization either with or without vacuum for a period of time (for example approximately 2 to 56 hours) at a selected temperature (such as at or above room temperature or below 50° C.) in order to remove the moisture in the coating.

The drying process improves integrity of the coating layer, protects loss of coating components during transit through body passages to the target treatment site, and improves drug absorption in the tissue. The moisture in the coating changes the balance of the hydrophilic and hydrophobic components in the coating. The moisture in the coating also accelerates release of the drug and additive in vivo and in vitro from the surface of the device. The moisture reduces drug retention during the delivery of the balloon catheter to the target site and accelerates drug loss during the initial phase of inflation of the balloon (or other inflatable component of the medical device). The loss of drug during the delivery and inflation decreases the amount of drug that remains and is available to be delivered at the target site. This can result in less than optimal, highly variable, and even less than therapeutic drug concentration levels in the tissue after deployment.

A drying step after sterilization removes moisture, decreases drug loss during transit, and increases drug levels in tissue after deployment. Perhaps equally important, by decreasing drug loss during transit, the drying step after sterilization decreases a major source of variability in tissue concentration levels of drug and thereby improves consistency of the therapeutic effect of the medical device. The removal of moisture is even more important when a large percentage of coating components are hydrophilic. A drying step after sterilization, optionally under vacuum and at a specific temperature between room temperature and 50° C., optimizes coating properties such that optimal and consistent therapeutic levels of drug are delivered to the tissue by the medical device.

Preparation

The medical device and the coating solution of embodiments of the present invention can be made according to various methods. For example, the coating solution can be prepared by dispersing, dissolving, diffusing, or otherwise mixing all the ingredients, such as a therapeutic agent, an additive, and a solvent, simultaneously together. Alternatively, the coating solution can be prepared by sequentially adding each component based on solubility or any other parameters. For example, the coating solution can be prepared by first adding the therapeutic agent to the solvent and then adding the additive. Alternatively, the additive can be added to the solvent first and then the therapeutic agent can be later added. If the solvent used does not sufficiently dissolve the drug, it is preferable to first add the additive to the solvent, then the drug, since the additive will increase drug solubility in the solvent. Alternatively, combinations of two or more solvents are used, for example, by combining two solvents prior to addition of drug and additive, or by adding drug to one solvent and additive to another solvent and then combining, or by adding only one of drug or additive to one solvent and then adding the second solvent and finally the other drug or additive.

In some cases, for example in the case of a protective top layer that is to be coated over a drug layer already deployed on the device (by methods of the present invention or by others), a drug may not be included in the coating solution, and the coating solution may essentially consist of solvent and additive.

Therapeutic Agent

The drugs or biologically active materials, which can be used in embodiments of the present invention, can be any therapeutic agent or substance. The drugs can be of various physical states, e.g., molecular distribution, crystal forms or cluster forms. Examples of drugs that are especially useful in embodiments of the present invention are lipophilic, substantially water insoluble drugs, such as paclitaxel, rapamycin, daunorubicin, doxorubicin, lapachone, vitamin D2 and D3 and analogues and derivatives thereof. These drugs are especially suitable for use in a coating on a balloon catheter used to treat tissue of the vasculature.

Other drugs that may be useful in embodiments of the present invention include, without limitation, glucocorticoids (e.g., dexamethasone, betamethasone), hirudin, angiopeptin, aspirin, growth factors, antisense agents, anti-cancer agents, anti-proliferative agents, oligonucleotides, and, more generally, anti-platelet agents, anti-coagulant agents, anti-mitotic agents, antioxidants, anti-metabolite agents, anti-chemotactic, and anti-inflammatory agents.

Also useful in embodiments of the present invention are polynucleotides, antisense, RNAi, or siRNA, for example, that inhibit inflammation and/or smooth muscle cell or fibroblast proliferation.

Anti-platelet agents for use in embodiments of the present invention can include drugs such as aspirin and dipyridamole. Aspirin is classified as an analgesic, antipyretic, anti-inflammatory and anti-platelet drug. Dipyridamole is a drug similar to aspirin in that it has anti-platelet characteristics. Dipyridamole is also classified as a coronary vasodilator. Anticoagulant agents for use in embodiments of the present invention can include drugs such as heparin, protamine, hirudin and tick anticoagulant protein. Anti-oxidant agents for use in embodiments of the present invention can include probucol. Anti-proliferative agents for use in embodiments of the present invention can include drugs such as amlodipine and doxazosin. Anti-mitotic agents and anti-metabolite agents that can be used in embodiments of the present invention include drugs such as methotrexate, azathioprine, vincristine, vinblastine, 5-fluorouracil, adriamycin, and mutamycin. Antibiotic agents for use in embodiments of the present invention include penicillin, cefoxitin, oxacillin, tobramycin, and gentamicin. Suitable antioxidants for use in embodiments of the present invention include probucol. Additionally, genes or nucleic acids, or portions thereof can be used as the therapeutic agent in embodiments of the present invention. Furthermore, collagen-synthesis inhibitors, such as tranilast, can be used as a therapeutic agent in embodiments of the present invention.

Photosensitizing agents for photodynamic or radiation therapy, including various porphyrin compounds such as porfimer, for example, are also useful as drugs in embodiments of the present invention.

Drugs for use in embodiments of the present invention also include everolimus, somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxycyclophosphamide, estramustine, melphalan, ifosfamide, trofosfamide, chlorambucil, bendamustine, dacarbazine, busulfan, procarbazine, treosulfan, temozolomide, thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, betulinic acid, camptothecin, lapachol, beta.-lapachone, podophyllotoxin, betulin, podophyllic acid 2-ethylhydrazide, molgramostim (rhuGM-CSF), peginterferon a-2b, lenograstim (r-HuG-CSF), filgrastim, macrogol, dacarbazine, basiliximab, daclizumab, selectin (cytokine antagonist), CETP inhibitor, cadherines, cytokinin inhibitors, COX-2 inhibitor, NFkB, angiopeptin, ciprofloxacin, camptothecin, fluoroblastin, monoclonal antibodies, which inhibit the muscle cell proliferation, bFGF antagonists, probucol, prostaglandins, 1,11-dimethoxycanthin-6-one, 1-hydroxy-11-methoxycanthin-6-one, scopoletin, coichicine, NO donors such as pentaerythritol tetranitrate and syndnoeimines, S-nitrosoderivatives, tamoxifen, staurosporine, beta.-estradiol, a-estradiol, estriol, estrone, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors (tyrphostines), cyclosporine A, 6-a-hydroxy-paclitaxel, baccatin, taxotere and other macrocyclic oligomers of carbon suboxide (MCS) and derivatives thereof, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, .beta.-sitosterin, ademetionine, myrtecaine, polidocanol, nonivamide, levomenthol, benzocaine, aescin, ellipticine, D-24851 (Calbiochem), colcemid, cytochalasin A-E, indanocine, nocodazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active agents from the group of antibiotics such as cefadroxil, cefazolin, cefaclor, cefotaxim, tobramycin, gentamycin, penicillins such as dicloxacillin, oxacillin, sulfonamides, metronidazol, antithrombotics such as argatroban, aspirin, abciximab, synthetic antithrombin, bivalirudin, coumadin, enoxaparin, desulphated and N-reacetylated heparin, tissue plasminogen activator, GpIIb/IIIa platelet membrane receptor, factor Xa inhibitor antibody, heparin, hirudin, r-hirudin, PPACK, protamin, prourokinase, streptokinase, warfarin, urokinase, vasodilators such as dipyramidole, trapidil, nitroprussides, PDGF antagonists such as triazolopyrimidine and seramin, ACE inhibitors such as captopril, cilazapril, lisinopril, enalapril, losartan, thiol protease inhibitors, prostacyclin, vapiprost, interferon a, .beta and y, histamine antagonists, serotonin blockers, apoptosis inhibitors, apoptosis regulators such as p65 NF-kB or Bcl-xL antisense oligonucleotides, halofuginone, nifedipine, tranilast, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, mutamycin, procainamide, retinoic acid, quinidine, disopyramide, flecamide, propafenone, sotalol, amidorone, natural and synthetically obtained steroids such as bryophyllin A, inotodiol, maquiroside A, ghalakinoside, mansonine, strebloside, hydrocortisone, betamethasone, dexamethasone, non-steroidal substances (NSAIDS) such as fenoprofen, ibuprofen, indomethacin, naproxen, phenylbutazone and other antiviral agents such as acyclovir, ganciclovir and zidovudine, antimycotics such as clotrimazole, flucytosine, griseofulvin, ketoconazole, miconazole, nystatin, terbinafine, antiprozoal agents such as chloroquine, mefloquine, quinine, moreover natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-a-senecioyloxychaparrin, taxamairin A and B, regenilol, triptolide, moreover cymarin, apocymarin, aristolochic acid, anopterin, hydroxyanopterin, anemonin, protoanemonin, berberine, cheliburin chloride, cictoxin, sinococuline, bombrestatin A and B, cudraisoflavone A, curcumin, dihydronitidine, nitidine chloride, 12-beta-hydroxypregnadien-3,20-dione, bilobol, ginkgol, ginkgolic acid, helenalin, indicine, indicine-N-oxide, lasiocarpine, inotodiol, glycoside 1a, podophyllotoxin, justicidin A and B, larreatin, malloterin, mallotochromanol, isobutyrylmallotochromanol, maquiroside A, marchantin A, maytansine, lycoridicin, margetine, pancratistatin, liriodenine, bisparthenolidine, oxoushinsunine, aristolactam-AII, bisparthenolidine, periplocoside A, ghalakinoside, ursolic acid, deoxypsorospermin, psychorubin, ricin A, sanguinarine, manwu wheat acid, methylsorbifolin, sphatheliachromen, stizophyllin, mansonine, strebloside, akagerine, dihydrousambarensine, hydroxyusambarine, strychnopentamine, strychnophylline, usambarine, usambarensine, berberine, liriodenine, oxoushinsunine, daphnoretin, lariciresinol, methoxylariciresinol, syringaresinol, umbelliferon, afromoson, acetylvismione B, desacetylvismione A, and vismione A and B.

A combination of drugs can also be used in embodiments of the present invention. Some of the combinations have additive effects because they have a different mechanism, such as paclitaxel and rapamycin, paclitaxel and active vitamin D, paclitaxel and lapachone, rapamycin and active vitamin D, rapamycin and lapachone. Because of the additive effects, the dose of the drug can be reduced as well. These combinations may reduce complications from using a high dose of the drug.

Additive

In certain embodiments of the present invention, the additive has two parts. One part is hydrophilic and the other part is a drug affinity part. The drug affinity part is a hydrophobic part and/or has an affinity to the therapeutic agent by hydrogen bonding and/or van der Waals interactions. The drug affinity part of the additive may bind the lipophilic drug, such as rapamycin or paclitaxel. The hydrophilic portion accelerates diffusion and increases permeation of the drug into tissue. The drug affinity part may include aliphatic and aromatic organic hydrocarbon groups, such as benzene, toluene, and alkanes, among others. These parts are not water soluble. They may bind both hydrophobic drug, with which they share structural similarities, and lipids of cell membranes. The hydrophilic part may include hydroxyl groups, amine groups, amide groups, carbonyl groups, carboxylic acid and anhydrides, ethyl oxide, ethyl glycol, polyethylene glycol, ascorbic acid, amino acid, amino alcohol, glucose, sucrose, sorbitan, glycerol, polyalcohol, phosphates, sulfates, organic salts and their substituted molecules, among others.

The additive in embodiments of the present invention is at least one of a surfactant, a polymer, and a chemical compound (MW<1300). In one embodiment, the chemical compound has one or more hydroxyl, amino, carbonyl, carboxyl, acid, amide or ester groups. In embodiments of the invention, the chemical compound is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In embodiments of the invention, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters and derivatives thereof.

In embodiments of the invention, the additive is chosen from p-isononylphenoxypolyglycidol, PEG laurate, PEG oleate, PEG stearate, PEG glyceryl laurate, Tween 20, Tween 40, Tween 60, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerols, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol, and penta(propylene glycol), poly(propylene glycol) oligomers, and derivatives and combinations thereof.

In embodiments of the invention, the polymer is one of polyolefins, polyisobutylene, ethylene-α-olefin copolymers, acrylic polymers and copolymers, polyvinyl chloride, polyvinyl methyl ether, polyvinylidene fluoride and polyvinylidene chloride, polyacrylonitrile, polyvinyl ketones, polystyrene, polyvinyl acetate, ethylene-methyl methacrylate copolymers, acrylonitrile-styrene copolymers, ABS resins, Nylon 12 and its block copolymers, polycaprolactone, polyoxymethylenes, polyesters, polyethers, polyamides, epoxy resins, polyurethanes, rayon-triacetate, cellulose, cellulose acetate, cellulose butyrate, cellophane, cellulose nitrate, cellulose propionate, cellulose ethers, carboxymethyl cellulose, chitins, polylactic acid, polyglycolic acid, polyethylene oxide, polylactic acid-polyethylene oxide copolymers, polyethylene glycol, polypropylene glycol, polyvinyl alcohol, polyvinylpyrrolidone, and mixtures and block copolymers thereof.

Solvents

In embodiments of the invention, solvents for preparing of the coating layer may include, as examples, any combination of one or more of the following: (a) water, (b) alkanes such as hexane, octane, cyclohexane, and heptane, (c) aromatic solvents such as benzene, toluene, and xylene, (d) alcohols such as methnol, ethanol, propanol, and isopropanol, diethylamide, ethylene glycol monoethyl ether, Trascutol, and benzyl alcohol (e) ethers such as dioxane, dimethyl ether and tetrahydrofuran, (f) esters/acetates such as ethyl acetate and isobutyl acetate, (g) ketones such as acetone, acetonitrile, diethyl ketone, and methyl ethyl ketone, and (h) mixture of water and organic solvents such as water/ethanol, water/acetone, water/methanol, water/ethanol/acetone, water/tetrahydrofuran.

Organic solvents, such as short-chained alcohol, dioxane, tetrahydrofuran, dimethylformamide, acetonitrile, dimethylsulfoxide, etc., are particularly useful and preferred solvents in embodiments of the present invention because these organic solvents generally disrupt collodial aggregates and co-solubilize all the components in the coating solution.

The therapeutic agent and additive or additives may be dispersed in, solubilized, or otherwise mixed in the solvent. The weight percent of drug and additives in the solvent may be in the range of 0.1 to 80% by weight, preferably 2 to 20% by weight.

Another embodiment of the invention relates to a method for preparing a medical device, particularly, for example, a balloon catheter or a stent. First, a coating solution or suspension comprising, for example, at least one solvent, at least one therapeutic agent, and at least one additive is prepared. In at least one embodiment, the coating solution or suspension includes only these three components. The content of the therapeutic agent in the coating solution can be from 0.5 to 50% by weight based on the total weight of the solution. The content of the additive in the coating solution can be from 1 to 45% by weight, 1 to 40% by weight, or from 1 to 15% by weight based on the total weight of the solution. The amount of solvent used depends on the coating process and viscosity. It will affect the uniformity of the drug-additive coating but will be evaporated after coating solution is applied.

In other embodiments, two or more solvents, two or more therapeutic agents, and/or two or more additives may be used in the coating solution.

Medical Device

Implantable and non-implantable medical devices may be coated using the methods and apparatus of the present invention. Examples of coated medical devices include a balloon catheter, a perfusion balloon catheter, an infusion catheter such as a distal perforated drug infusion tube, a perforated balloon, a spaced double balloon, a porous balloon, a weeping balloon, a cutting balloon catheter, a scoring balloon catheter, a laser catheter, an atherectomy device, a debulking catheter, a stent, a filter, a stent graft, a covered stent, a patch, a wire, a valve, leads or implantable pulse generators, pacers or neurostimulators, among others. In one embodiment, the methods and apparatuses of the present invention are especially useful for coating continuous surfaces on medical devices, since continuous flowing of the coating composition over the surface of the medical devices is involved. Medical devices with continuous surfaces include a balloon catheter, a perfusion balloon catheter, an infusion catheter such as a distal perforated drug infusion tube, a perforated balloon, a porous balloon, and a weeping balloon, a cutting balloon catheter, a scoring balloon catheter, a stent graft, a covered stent, a patch, a wire, and leads for pacing, sensing, and defibrillation.

In one embodiment of balloon catheters, the balloon diameter is in the range of 1.0 mm to 40 mm. In another embodiment of the PTCA balloon catheters, the balloon diameter is in the range of 1.0 mm to 5.0 mm in 0.25 mm increments. In another embodiment of PTA balloon catheters, the balloon diameter is in the range of 2.0 mm to 12.0 mm. In one embodiment of non vascular balloon catheters, the balloon diameter is in the range of 2.0 mm to 40 mm.

In one embodiment of balloon catheters, the balloon length is in the range of 5.0 mm to 300 mm. In another embodiment of the PTCA balloon catheters, the balloon length is in the range of 8.0 mm to 40.0 mm. In another embodiment of PTA balloon catheters, the balloon length is in the range of 8.0 mm to 300.0 mm. In one embodiment of non vascular balloon catheters (for example, gastric and respiratory applications), the balloon length is in the range of 10.0 mm to 200 mm.

Dispensing System

Dispensing systems in embodiments of the invention comprise a coating solution container, a metering dispenser, a dispenser tip, and a programmable controller. The metering dispenser includes a syringe pump, a micro-metering pump, a dispensing pipette, and an automatic metering pump system. The metering dispenser is able to dispense from 1 μL to 1000 μL. A dispensing tip is connected to the metering dispenser for easy coating application. The dispensing tip typically includes a hub and a tip. The hub is connected to the metering dispenser. The tip is used to apply coating on the medical device either by contact or non-contact. The tip opening can have different shapes including, but not limited to, circular, oval, square, and rectangular. The diameter of the tip opening ranges from about 10 micron-meters to about 3 mm, for example from about 50 micro-meters to about 500 micro-meters, or from about 0.05 mm to about 2 mm. The length of the dispensing tip ranges from about 5 mm to about 70 mm, for example from about 10 mm to about 30 mm, or from about 30 mm to about 50 mm. The tip can be straight or with an angle (e.g., 135°, 45° or 90°) and the tip can be rigid or flexible. The tip can be tapered, non-tapered, Teflon-lined, Teflon-coated, Teflon-lined and crimped, or the tip can be a brush. The dispensing tip can be made of metals, metal alloys, metal with a polymer coating or lining. For example, the dispensing tip can be made of stainless steel, polyethylene, polypropylene, polyesters, polyamides, polyurethanes, PTFE, and/or metal with a PTFE coating or lining.

There are many kinds of pipettes from various manufacturers, such as Brinkman Eppendorf research pipette, Fisherbrand finnpipette pipette, Corning Lambda pipette, Wheaton Socorex Acura micropipetter and Hamilton SoftGrip pipette. One preferable pipette in embodiments of the invention is the digital single channel air displacement pipette. The adjustable volume ranges from 0.02 ml to 10 ml. The fast-dial system allows 0.1 μl fine adjustment. The dispensing also can be done with a stepper pipette, such as Finnpipette Stepper pipette from Thermo Electron and Brand HandyStep repeating pipette from BrandTech. The electronic micropipetters can be used in embodiments of the invention according to the volume to be used. The pipette tips can be used as the dispensing tips in all of dispensing systems.

The syringe pump can be also used for this application. There are both single channel and multiple channel syringe pumps, for example, Cole-Parmer single-syringe infusion pump features microprocessor motor control and precision gearing. The flow rate can be as low as 0.2 μl/hr. The accuracy can be as low as ±0.5%, and reproducibility can be as low as ±0.2%. The syringe size can be from 10 μl to 60 ml.

A programmable dispensing system may use precision stepper motors to control ceramic piston pumps. This type of programmable dispensing system can dispense from 500 nanoliters per dispense to 0.5 liters per minute continuous flow. It has single and dual channel flow configuration. One example of a programmable dispensing system is a Sensata programmable dispensing system from Fluid metering, Inc. Another example is the automatic metering system from IVEK Corporation. It includes a dispensing controller module, micro linear, pump module and other accessories. The controller modules single channel, microprocessor-based units contain all the control, monitoring, and interface components. The controller provides very accurate and precise fluid dispensing and metering. The micro linear pump module is comprised of a ceramic piston fabrication and mated ceramic cylinder installed into a case with intake and discharge ports. The micro linear pump sizes include several models, for an example, 20 μl chamber, 0.010 μl resolution, 50 μl chamber, 0.025 μl resolution, 100 μl chamber, 0.050 μl resolution, and 200 μl chamber, 0.100 μl resolution.

Rotation and Transverse Movement Assembly

The rotation and transverse movement assembly is to provide linear and rotation movement during the solution dispensing and after solution dispensing. During dispensing, the device to be coated, dispensing tip or both can move transversely or rotationally. After dispensing, only the device to be coated moves transversely and rotationally. The linear speed, distance and rotation speed are controlled to achieve the best coating quality. The rotation speed is in the range of 0.1 to 10 revolutions per second, preferably from 0.5 to 5 revolutions per second, most preferably from 0.8 to 2 revolutions per second. The linear or transverse speed is the range of from 0.1 to 100 mm per second, preferably from 1 to 75 mm per second, most preferably from 2 to 50 mm per second. The dispensing time is in the range of from 2 to 300 seconds, preferably from 5 to 120 seconds, which depends on the dispensing coating volume and diameters (1.5 mm to 12 mm) and lengths (5 to 200 mm) of the balloon catheters. After the dispensing of the coating solution on the balloon, the coating solution flows and solidifies on the surface of the balloon during the transverse and rotational motion of the device to be coated. The flowing of the coating leads to a more uniform coating on the surface of the device. The time of flowing and solidification of the coating on the balloon after dispensing of the liquid coating is in the range of from 0.1 to 10 minutes, preferably from 0.5 to 5 minutes. The coated balloon catheters are then dried at room temperature for 12 to 24 hours. The balloon catheters are then folded, rewrapped, packaged, and sterilized under ethylene oxide.

EXAMPLES

The following examples include embodiments of medical devices and coating layers within the scope of the present invention. While the following examples are considered to embody the present invention, the examples should not be interpreted as limitations upon the present invention.

Example 1

Preparation of coating solutions: 70 mg of Octanoyl-N-methylglucamide was added into 1.0 ml of solvent mixture (50% acetone and 50% ethanol). Then, 35 mg of paclitaxel was added into the solution. The solution was mixed at room temperature until a homogeneous solution was obtained.

A PTCA balloon catheter (3.5 mm in diameter and 20 mm in length) was inflated at 2 atm. A pipette (Fisher Scientific, Finnpipette 5-50 μl) was used to pipette 25 μl of solution, and then the solution was transferred onto the inflated 3.5 mm×20 mm balloon catheter. The solution was flowing on the surface of the balloon while the balloon was moving both circumferentially and longitudinally. The time of flowing and evaporation of the solvent and solidification of the coating is about 1 minute after the dispensing of the coating solution on the surface of the balloon catheter. The residual solvent was evaporated and the coating was dried at room temperature for 12 hours. The balloon was folded, rewrapped and packaged, then sterilized with ethylene oxide. The drug loading was 3.75 μg/mm$^2$ from HPLC analysis.

The coated PTCA balloon catheter was inserted into a target site in the coronary vasculature (LAD, LCX and RCA) of a 25 to 45 kg pig. The balloon was inflated to approximately 12 atm. The overstretch ratio (the ratio of balloon diameter to vessel diameter) was about 1.15 to 1.20. The drug was delivered into the target tissue during 30 to 60 seconds of inflation. The balloon catheter was then deflated and was withdrawn from animal body. The target blood vessel was harvested 0.25 to 24 hours after the procedure. The drug content in the target tissue and the residual drug remaining on the balloon were analyzed by tissue extraction and HPLC.

In chronic animal tests, angiography was performed before and after all interventions and at 28 days after the procedure. In some cases, a stent was first crimped on the coated balloon catheter and deployed by the coated catheter into a target site of the coronary vasculature. Luminal diameters were measured and late lumen loss was calculated. Late lumen loss is the difference between the minimal lumen diameter measured after a period of follow-up time (usually weeks to months after an intervention, such as angioplasty and stent placement in the case of this example) and the minimal lumen diameter measured immediately after the intervention. Restenosis is quantified by the diameter stenosis, which is the difference between the mean lumen diameters at follow-up and immediately after the procedure divided by the mean lumen diameter immediately after the procedure. The animal test results are reported below. All data is an average of five or six experimental data points.

After the procedure, the residual drug on the balloon was 13.7 μg. The drug content in tissue harvested 60 minutes after the procedure was 45.2 μg. When the drug coated balloon was used to deploy a pre-crimped bare metal stent, the late lumen loss after 28 days was 0.49 mm (STDEV 0.26 mm). The diameter stenosis was 11.3%.

Example 2

Preparation of coating solutions: 35 mg of Octanoyl-N-methylglucamide and 35 mg of Tween 20 were added into 1.0 ml of solvent mixture (50% acetone and 50% ethanol). Then, 35 mg of paclitaxel was added into the solution. The solution was mixed at room temperature until a homogeneous solution was obtained.

A PTCA balloon catheter (3.5 mm in diameter and 20 mm in length) was inflated at 2 atm. A pipette (Fisher Scientific, Finnpipette 5-50 μl) was used to pipette 23 μl of solution (volume calibrated for dispensing of 660 μg drug), and then the solution was transferred onto the inflated 3.5 mm×20 mm balloon catheter and the solution was flowing on the surface of the balloon while the balloon was moving both circumferentially and longitudinally. The time of flowing and solvent evaporation and solidification of the coating is about 1 minute after the dispensing of the coating solution on the surface of the balloon catheter. The residual solvents were evaporated and the coating was dried at room temperature for 12 hours. The balloon was folded, rewrapped and packaged, then sterilized with ethylene oxide. The drug loading was 3.08 μg/mm² from HPLC analysis.

The animal tests and measurements are the same as in the Example 1. After the procedure, the residual drug on the balloon was 21.3 μg. The drug content in tissue harvested 60 minutes after the procedure was 42.2 μg. The late lumen loss after 28 days was 0.3 mm (STDEV 0.23 mm). The diameter stenosis is 5.4%.

Example 3

Preparation of base layer coating solutions: 35 mg of lactobionic acid and 10 mg of diethanolamine were added into 1.0 ml of solvent mixture (25% water, 37.5% acetone and 37.5% ethanol). Then, 35 mg of paclitaxel was added into the solution. The solution was mixed at room temperature or at 50° C. until a homogeneous solution was obtained.

Preparation of top layer coating solutions: 35 mg of methylparaben was added into 1.0 ml of acetone. The solution was mixed at room temperature until a homogeneous solution was obtained.

A PTCA balloon catheter (3.5 mm in diameter and 20 mm in length) was inflated at 2 atm. A pipetter (Fisher Scientific, Finnpipette 5 to 50 μl) was used to pipette 25 μl of solution (volume calibrated for dispensing of 770 μg drug), and then the solution was transferred onto the inflated 3.5 mm×20 mm balloon catheter and the solution was flowing on the surface of the balloon while the balloon was moving both circumferentially and longitudinally. The solvents were evaporated and the coating was dried at room temperature for 12 hours. After the base layer coating was dried, the catheter was inflated again at 1.5 to 3 atm. A pipette (Fisher Scientific, Finnpipette 5 to 50 μl) was used to pipette 25.0 μl of top layer coating solution, and then the solution was transferred onto the 3.5 mm×20 mm balloon catheter while the balloon was moving both circumferentially and longitudinally. The time of flowing and solvent evaporation and solidification of the coating is about 1 minute after the dispensing of the coating solution on the surface of the balloon catheter. The residual solvent was evaporated and the coating was dried at room temperature for 12 hours. After the top layer coating was dried, the balloon was folded, rewrapped and packaged, then sterilized with ethylene oxide. The drug loading was 3.68 μg/mm² from HPLC analysis.

The animal tests and measurements are the same as in the Example 1. After the procedure, the residual drug on the balloon was 44.4 μg. The drug content in tissue harvested 15 minutes after the procedure was 22.96 μg.

Example 4

Preparation of coating solutions: 70 mg of Octanoyl-N-methylglucamide was added into 1.0 ml of solvent mixture (50% acetone and 50% ethanol). Then, 35 mg of paclitaxel was added into the solution. The solution was mixed at room temperature until a homogeneous solution was obtained.

A balloon catheter (6.0 mm in diameter and 40 mm in length) was inflated at 2 atm. A pipetter (Fisher Scientific, Finnpipette 10 to 100 μl) was used to pipette 90 μl of solution, and then the solution was transferred onto the inflated 6.0 mm×40 mm balloon catheter and the solution was flowing on the surface of the balloon while the balloon was moving both circumferentially and longitudinally. The time of flowing and solvent evaporation and solidification of the coating is about 1 minute after the dispensing of the coating solution on the surface of the balloon catheter. The coating was dried at room temperature for 12 hours. The balloon was folded, rewrapped and packaged, then sterilized with ethylene oxide.

Example 5

Preparation of coating solutions: 35 mg of gluconolactone was added into 1.0 ml of solvent mixture (20% water, 40% acetone and 40% ethanol). Then, 35 mg of paclitaxel was added into the solution. The solution was mixed at room temperature or at 50° C. until a homogeneous solution was obtained.

Twenty-four PTCA balloon components (3.5 mm in diameter and 20 mm in length) were used for the repeatability test. Each balloon was coated with a pipette (Fisher Scientific, Finnpipette 5 to 50 µl) by transferring 22 µl of solution (volume calibrated for 660 µg drug) onto the balloon and the solution was flowing on the surface of the balloon while the balloon was moving both circumferentially and longitudinally. The time of flowing and evaporation of solvent and solidification of the coating is about 1 minute after the dispensing of the coating solution on the surface of the balloon catheter. Residual solvents were evaporated and the coating was dried at room temperature for 12 hours. The drug loading of each balloon was analyzed by HPLC. The average drug loading was 644.78 µg and the relative standard deviation was 5.2%. The excellent precision allows for easy calibration of pipette or meter volume to adjust for measurement errors during solution preparation.

Example 6

Preparation of coating solutions: 10 mg of gluconolactone was added into 1.0 ml of solvent mixture (20% water, 40% acetone and 40% ethanol). Then, 15.5 mg of paclitaxel was added into the solution. The solution was mixed at room temperature until a homogeneous solution was obtained.

Ten PTCA balloon catheters (3.0 mm in diameter and 20 mm in length) were used for the repeatability test. Each balloon catheter was inflated and coated with a pipette (Fisher Scientific, Finnpipette 5 to 50 µl) by transferring 21.5 µl of solution onto the balloon. The solution was flowing on the surface of the balloon while the balloon was moving both circumferentially and longitudinally. The time of flowing and solvent evaporation and solidification of the coating is about 1 minute after the dispensing of the coating solution on the surface of the balloon catheter. The residual solvents were evaporated and the coating was dried at room temperature for 12 hours. After the first layer coating was dried, the catheter was inflated again at 1.5 to 3 atm. A pipette (Fisher Scientific, Finnpipette 5 to 50 µl) was used to pipette 21.5 µl of coating solution, and then the solution was transferred onto the 3.0 mm×20 mm balloon catheter while the balloon was moving both circumferentially and longitudinally. The solvent was evaporated and the coating was dried at room temperature for 12 hours. After the second layer coating was dried, the balloon was folded, rewrapped and packaged, then sterilized with ethylene oxide. The drug loading on each catheter was analyzed by HPLC. The average drug loading was 648.52 µg and the relative standard deviation was 5.1%. The expected drug load from two applications of 21.5 µl solution containing 15.5 mg/ml paclitaxel is 666.5 µg, demonstrating accuracy of greater than 97% for the coating method.

Similar results are expected when the coating formulation is applied to the balloon surface using a rotating and transverse movement apparatus in accordance with embodiments of the present invention.

Example 7

Twelve PTCA balloon catheters (3.0 mm in diameter and 20 mm in length) were loaded with the coating solution of Example 1 (creating a first coating layer). The desired amount of drug (3 µg/mm$^2$) was obtained on the balloon surface.

A formulation for a top coating layer was then prepared. The formulation of the top coating layer was Tween 20 in acetone. 0.7 mg of the top coating formulation was coated over the first coating layer on twelve balloon surfaces. The coated balloons were dried. The catheters were sterilized under standard ethylene oxide sterilization. After sterilization, six of the PTCA balloon catheters were dried under vacuum at 45° C. for 24 hours. The other six PTCA balloon catheters, which served as the control, were not dried. The results showed that the adhesion of the coating on the surface of the balloon is improved with vacuum dry after sterilization. In addition, retention of the coating is improved in experiments in which the coated balloon is floated in a porcine aorta, and the drug absorption into vessel wall tissue is improved as well.

Example 8

Three hundred PTCA balloon catheters (2.5 mm in diameter and 18 mm in length) were used for the test. Each balloon catheter was inflated and coated with a semi-automatic coater by dispensing 16 µl of solution (volume calibrated for dispensing 300 µg target drug) onto the balloon. The solution flowed on the surface of the balloon while the balloon was moving both circumferentially and longitudinally. The time of flow and solvent evaporation and solidification of the coating was about 1 minute after the dispensing of the coating solution on the surface of the balloon catheter. The residual solvents were evaporated, and the coating was dried at room temperature for 12 hours. After the coating was dried, the balloon was folded, rewrapped and packaged, then sterilized with ethylene oxide. The catheters were vacuum dried after sterilization. Then, ten catheters were randomly taken from the three-hundred catheters for analysis. The drug loading on each catheter was analyzed by HPLC and listed in the following table.

|  | catheters | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| Drug loading (µg) | 300.7 | 280.9 | 296.3 | 292.8 | 268.5 | 284.8 | 312.0 | 299.2 | 298.4 | 299.6 |

The average drug loading was 293.3 µg, and relative standard deviation was 4.2%.

The numerical values set forth in the Example are reported as precisely as possible. The numerical values, however, inherently contain some imprecision necessarily resulting from the standard deviation found in their respective testing measurements, e.g., sample weighing, solution preparation, and sample analysis.

Example 9

Three hundred PTCA balloon catheters (3.0 mm in diameter and 18 mm in length) were used for the test. Each balloon catheter was inflated and coated with a semi-automatic coater by dispensing 19 μl of solution (volume calibrated for dispensing 350 μg target drug) onto the balloon. The solution was flowed on the surface of the balloon while the balloon was moving both circumferentially and longitudinally. The time of flow and solidification of the coating was about 1 minute after the dispensing of the coating solution on the surface of the balloon catheter. Residual solvents were evaporated, and the coating was dried at room temperature for 12 hours. After the coating was dried, the balloon was folded, rewrapped and packaged, then sterilized with ethylene oxide. The catheters were vacuum dried after sterilization. Then, ten catheters were randomly taken from the three-hundred catheters for analysis. The drug loading on each catheter was analyzed by HPLC and listed in the following table.

|  | catheters | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| Drug loading (μg) | 347.0 | 369.3 | 351.4 | 365.0 | 359.3 | 362.6 | 339.3 | 335.7 | 352.3 | 305.7 |

The average drug loading was 348.8 μg, and relative standard deviation was 5.3%.

The numerical values set forth in the Example are reported as precisely as possible. The numerical values, however, inherently contain some imprecision necessarily resulting from the standard deviation found in their respective testing measurements, e.g., sample weighing, solution preparation, and sample analysis.

Example 10

Three hundred PTCA balloon catheters (2.5 mm in diameter and 30 mm in length) were used for the test. Each balloon catheter was inflated and coated with a semi-automatic coater by dispensing 26 μl of solution (volume calibrated for dispensing 490 μg target drug) onto the balloon. The solution was flowed on the surface of the balloon while the balloon was moving both circumferentially and longitudinally. The time of flow and solidification of the coating was about 1 minute after the dispensing of the coating solution on the surface of the balloon catheter. Residual solvents were evaporated, and the coating was dried at room temperature for 12 hours. After the coating was dried, the balloon was folded, rewrapped and packaged, then sterilized with ethylene oxide. The catheters were vacuum dried after sterilization. Then, ten catheters were randomly taken from the three-hundred catheters for analysis. The drug loading on each catheter was analyzed by HPLC and listed in the following table.

|  | catheters | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| Drug loading (μg) | 492.6 | 474.7 | 490.0 | 497.7 | 496.9 | 507.9 | 503.0 | 495.2 | 488.5 | 505.0 |

The average drug loading was 495.2 μg, and relative standard deviation was 1.9%.

The numerical values set forth in the Example are reported as precisely as possible. The numerical values, however, inherently contain some imprecision necessarily resulting from the standard deviation found in their respective testing measurements, e.g., sample weighing, solution preparation, and sample analysis.

Example 11

Three hundred PTCA balloon catheters (3.0 mm in diameter and 30 mm in length) were used for the test. Each balloon catheter was inflated and coated with a semi-automatic coater by dispensing 31 μl of solution (volume calibrated for dispensing of 570 μg target drug) onto the balloon. The solution was flowed on the surface of the balloon while the balloon was moving both circumferentially and longitudinally. The time of flow and solidification of the coating was about 1 minute after the dispensing of the coating solution on the surface of the balloon catheter. The solvents were evaporated, and the coating was dried at room temperature for 12 hours. After the coating was dried, the balloon was folded, rewrapped and packaged, then sterilized with ethylene oxide. The catheters were vacuum dried after sterilization. Then, ten catheters were randomly taken from the three-hundred catheters for analysis. The drug loading on each catheter was analyzed by HPLC and listed in the following table.

| catheters | | | | | | | | | |
|---|---|---|---|---|---|---|---|---|---|
| 1 | 2 | 3 | 4 | 5 | 6 | 7 | 8 | 9 | 10 |
| Drug loading (µg) 549.5 | 610.7 | 596.1 | 547.7 | 569.7 | 564.6 | 594.7 | 587.2 | 593.2 | 599.1 |

The average drug loading was 581.3 µg, and relative standard deviation was 3.8%.

The numerical values set forth in the Example are reported as precisely as possible. The numerical values, however, inherently contain some imprecision necessarily resulting from the standard deviation found in their respective testing measurements, e.g., sample weighing, solution preparation, and sample analysis.

Example 12

Five PTCA balloon catheters (2.25 mm in diameter and 40 mm in length) and five PTCA balloon catheters (4.0 mm in diameter and 40 mm in length) were coated using the method described in Example 11. Each balloon catheter was inflated and coated with a calibrated volume of drug solution using a semi-automatic coater. The solution was flowed on the surface of the balloon while the balloon was moving both circumferentially and longitudinally. The time of flow and solidification of the coating is about 1 minute after the dispensing of the coating solution on the surface of the balloon catheter. The residual solvents were evaporated, and the coating was dried at room temperature for 12 hours. Each balloon on the catheter was cut into three equal sections, and drug on each section was analyzed by HPLC and listed in the following tables, demonstrating uniformity of the coating across segments of the coated balloon catheter.

| Balloon (2.25 mm × 40 mm) Number | Section | Percent of Coating |
|---|---|---|
| 1 | S1 | 37.2% |
|   | S2 | 36.1% |
|   | S3 | 26.7% |
| 2 | S1 | 34.4% |
|   | S2 | 32.5% |
|   | S3 | 33.1% |
| 3 | S1 | 37.4% |
|   | S2 | 32.5% |
|   | S3 | 30.2% |
| 4 | S1 | 33.2% |
|   | S2 | 36.8% |
|   | S3 | 30.0% |
| 5 | S1 | 32.4% |
|   | S2 | 36.7% |
|   | S3 | 30.9% |

| Balloon (4.0 mm × 40 mm) Number | Section | Percent of Coating |
|---|---|---|
| 1 | S1 | 28.2% |
|   | S2 | 30.4% |
|   | S3 | 41.3% |
| 2 | S1 | 34.0% |
|   | S2 | 30.0% |
|   | S3 | 36.0% |
| 3 | S1 | 27.5% |
|   | S2 | 29.9% |
|   | S3 | 42.6% |
| 4 | S1 | 31.3% |
|   | S2 | 31.5% |
|   | S3 | 37.2% |
| 5 | S1 | 35.2% |
|   | S2 | 29.2% |
|   | S3 | 35.6% |

What is claimed is:

1. An apparatus for dispensing a coating solution onto a surface of a balloon of a balloon catheter, the balloon catheter having a longitudinal axis that defines a longitudinal direction along the longitudinal axis, the apparatus comprising:
    a metering dispenser connected to a dispensing tip that dispenses the coating solution onto the surface of the balloon by contact or non-contact;
    a coating solution storage container that supplies the coating solution to the metering dispenser;
    a movement assembly that rotates the balloon catheter about the longitudinal axis and translocates the balloon catheter, the dispensing tip, or both back and forth in the longitudinal direction; and
    a controller that coordinates the dispensing of the coating solution through the metering dispenser with the rotation and translocation of the balloon catheter by the movement assembly,
wherein:
    the dispensing tip comprises a hub portion connected to the metering dispenser and a tip portion connected to the hub portion;
    the tip portion comprises a tip opening through which the coating solution is dispensed; and
    the dispensing tip further comprises a flexible tail connected to the tip portion, such that coating solution flows from the tip opening along the flexible tail to the surface of the balloon.

2. The apparatus according to claim 1, wherein the metering dispenser comprises at least one of a syringe, a syringe pump, a metering pipette, and an automatic metering system.

3. The apparatus according to claim 1, wherein the movement assembly concurrently rotates the balloon catheter about the longitudinal axis at a uniform tangential speed and translocates the balloon catheter, the dispensing tip, or both back and forth in the longitudinal direction at a uniform frequency.

4. The apparatus according to claim 1, wherein the movement assembly concurrently rotates the balloon catheter about the longitudinal axis and translocates only the dispensing tip back and forth in the longitudinal direction.

5. The apparatus according to claim 1, wherein the movement assembly concurrently rotates the balloon catheter about the longitudinal axis and translocates only the balloon catheter back and forth in the longitudinal direction.

6. The apparatus according to claim 1, wherein the movement assembly concurrently rotates the balloon catheter about the longitudinal axis and translocates both the balloon catheter and the dispensing tip back and forth in the longitudinal direction.

7. The apparatus according to claim 1, wherein the diameter of the tip opening is from 0.05 mm to 2 mm and the length of the dispensing tip is from 5 mm to 30 mm.

8. The apparatus according to claim 1, wherein the flexible tail contacts the surface of the balloon when the coating solution is dispensed to the surface of the balloon.

9. The apparatus according to claim 1, wherein the flexible tail is attached to an outer side of the tip portion of the dispensing tip.

10. The apparatus according to claim 1, wherein the flexible tail is threaded through the tip opening of the tip portion.

11. The apparatus according to claim 1, wherein the balloon is selected from the group consisting of a perforated balloon, a porous balloon, a spaced double balloon, and a weeping balloon.

12. The apparatus according to claim 1, wherein the balloon catheter is selected from the group consisting of a perfusion balloon catheter, a cutting balloon catheter, and a scoring balloon catheter.

* * * * *